(12) United States Patent
Casey et al.

(10) Patent No.: US 7,018,372 B2
(45) Date of Patent: Mar. 28, 2006

(54) CATHETER

(75) Inventors: Brendan Casey, Dublin (IE); Avril O'Higgins, Galway (IE); Eamon Brady, Elphin (IE); Patrick Griffin, Castlegar (IE)

(73) Assignee: Salviac Limited, (IE)

( * ) Notice: Subject to any disclaimer, the term of this patent is extended or adjusted under 35 U.S.C. 154(b) by 276 days.

(21) Appl. No.: 10/123,530

(22) Filed: Apr. 17, 2002

(65) Prior Publication Data

US 2003/0004493 A1    Jan. 2, 2003

(30) Foreign Application Priority Data

Apr. 17, 2001    (IE)    ................... 2001/0377

(51) Int. Cl.
*A61M 25/00*    (2006.01)

(52) U.S. Cl. ..................................... 604/524

(58) Field of Classification Search ................ 604/523, 604/524, 525, 526, 527
See application file for complete search history.

(56) References Cited

U.S. PATENT DOCUMENTS

| 3,498,286 | A | * | 3/1970 | Koester et al. ............. 600/325 |
| 4,776,844 | A | * | 10/1988 | Ueda ....................... 604/95.05 |
| 5,019,057 | A | * | 5/1991 | Truckai ....................... 604/527 |
| 5,176,660 | A | * | 1/1993 | Truckai ....................... 604/527 |
| 5,364,357 | A | * | 11/1994 | Aase ....................... 604/103.09 |
| 5,453,099 | A | * | 9/1995 | Lee et al. .................... 604/524 |
| 5,456,674 | A | * | 10/1995 | Bos et al. ................... 604/526 |
| 5,460,608 | A | | 10/1995 | Lodin et al. |
| 5,464,394 | A | | 11/1995 | Miller et al. |
| 5,551,444 | A | | 9/1996 | Finlayson |
| 5,571,085 | A | | 11/1996 | Accisano, III |
| 5,690,613 | A | | 11/1997 | Verbeek |
| 5,755,707 | A | * | 5/1998 | Miyagawa et al. ...... 604/103.1 |
| 5,885,227 | A | | 3/1999 | Finlayson |
| 5,976,120 | A | | 11/1999 | Chow et al. |
| 6,017,335 | A | | 1/2000 | Burnham |
| 6,022,343 | A | | 2/2000 | Johnson et al. |
| 6,080,488 | A | | 6/2000 | Hostettler et al. |
| 6,110,164 | A | * | 8/2000 | Vidlund ...................... 604/524 |
| 6,146,814 | A | | 11/2000 | Millet |
| 6,152,909 | A | | 11/2000 | Bagaoisan et al. |
| 6,171,295 | B1 | | 1/2001 | Garabedian et al. |
| 6,248,122 | B1 | | 6/2001 | Klumb et al. |

FOREIGN PATENT DOCUMENTS

DE    41 37 132 A1    5/1993

(Continued)

*Primary Examiner*—Manuel Mendez
(74) *Attorney, Agent, or Firm*—Kudirka & Jobse, LLP

(57) ABSTRACT

A catheter 1 suitable for advancement through a body passageway of a patient. The catheter 1 comprises a catheter body 4 which is flexible to provide the necessary trackability for the catheter 1 to advance through a body passageway, and two stainless steel reinforcement wires 5 extending along the catheter body 4 which provide the necessary pushability to advance the catheter 1 through the passageway. The reinforcements 5 are positioned diametrically opposed to one another by approximately 180 degrees on opposite sides of the longitudinal axis of the catheter 1, and the catheter body 4 is relatively soft and twistable. This configuration enables the entire catheter 1 to spontaneously twist during advancement so that the reinforcements 5 orientate themselves along a plane of neutral bending during advancement of the catheter 1. In this way, any resistance to the trackability of the catheter 1 due to the stiff reinforcements 5 is minimized.

93 Claims, 27 Drawing Sheets

FOREIGN PATENT DOCUMENTS

| | | |
|---|---|---|
| EP | 0 420 486 A1 | 4/1991 |
| EP | 0 829 271 A2 | 3/1998 |
| EP | 0 861 674 A1 | 9/1998 |
| EP | 1025813 A | 8/2000 |
| EP | 1 088 570 A1 | 4/2001 |
| WO | WO 95/24236 | 9/1995 |

* cited by examiner

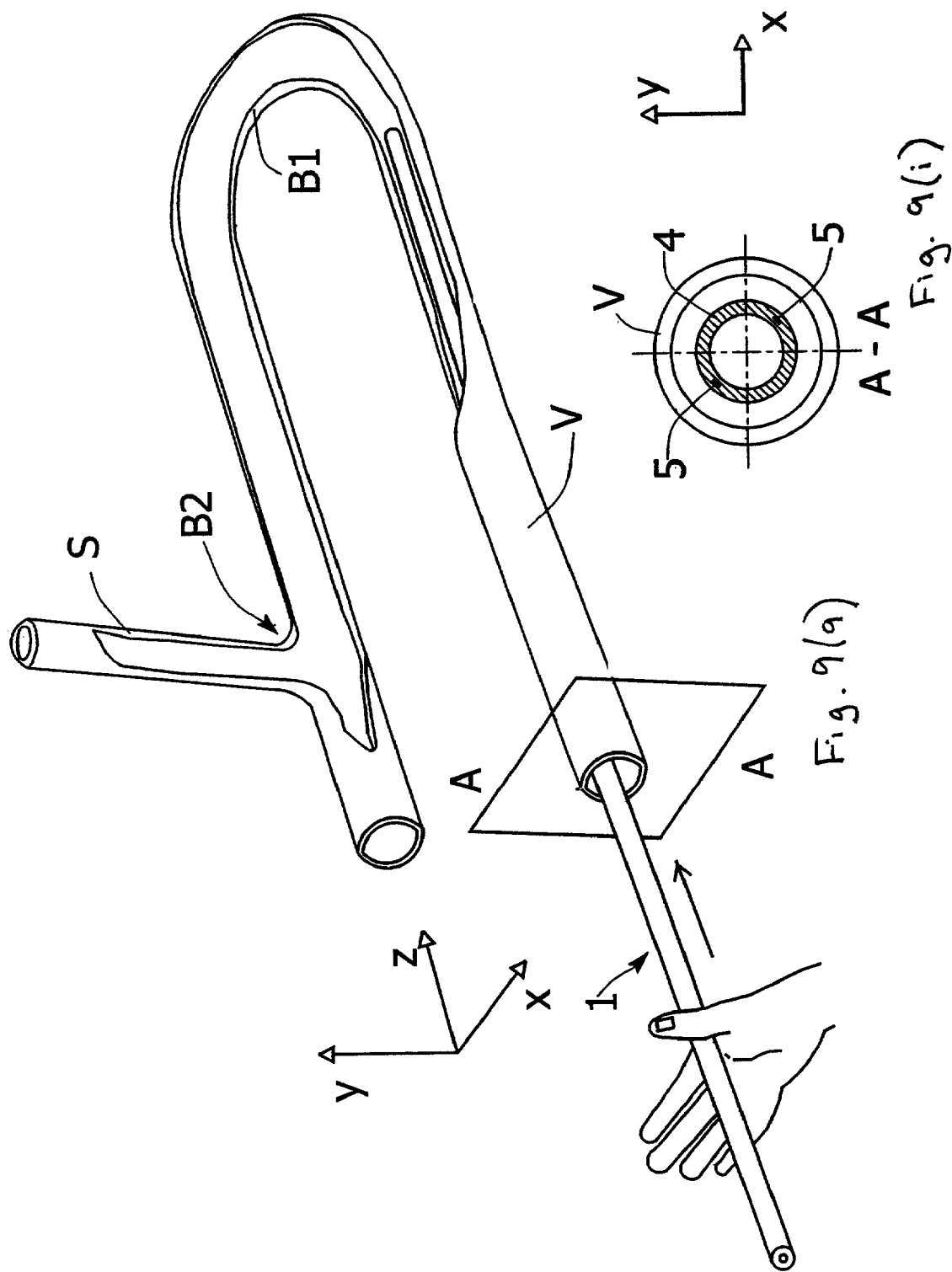

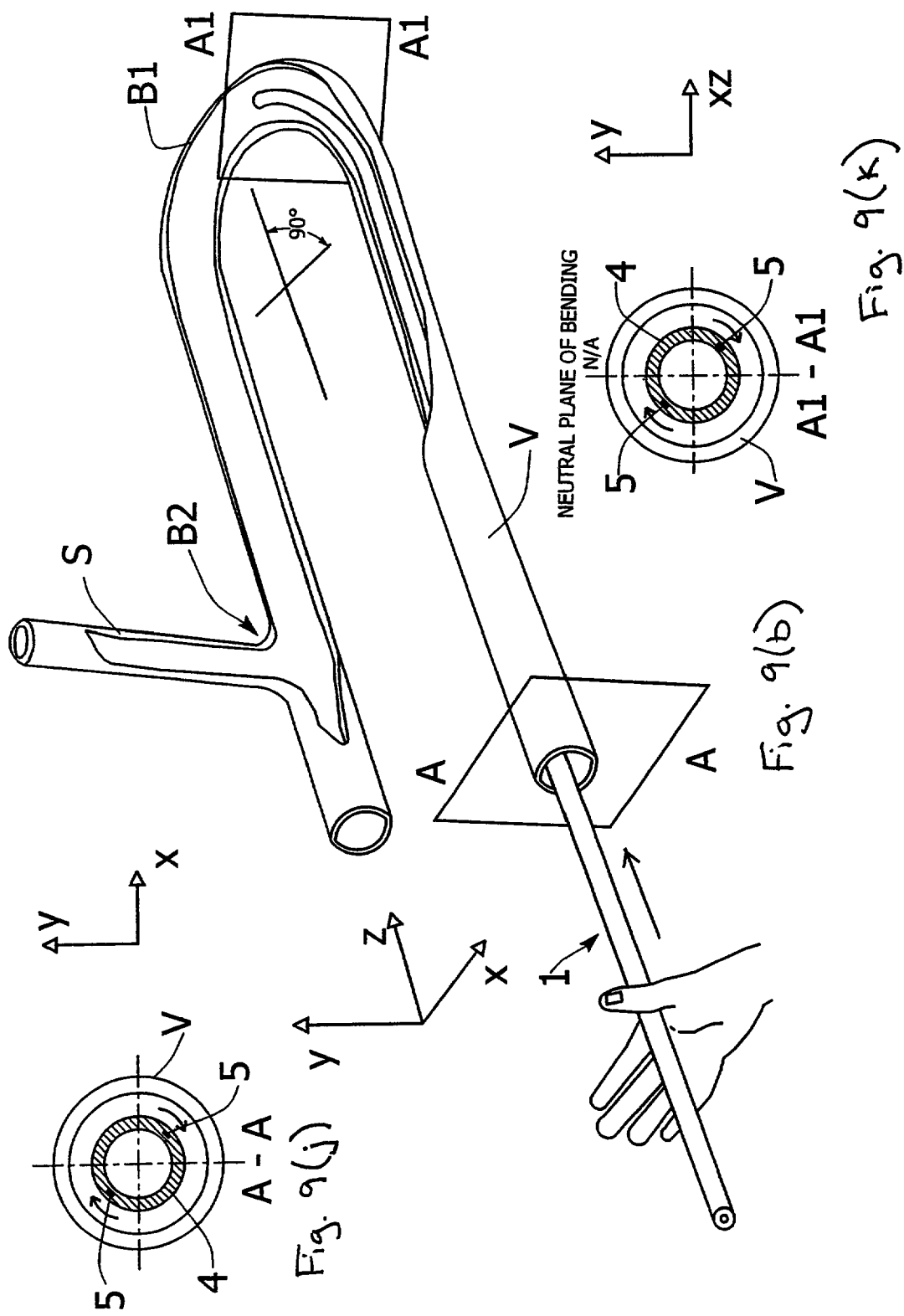

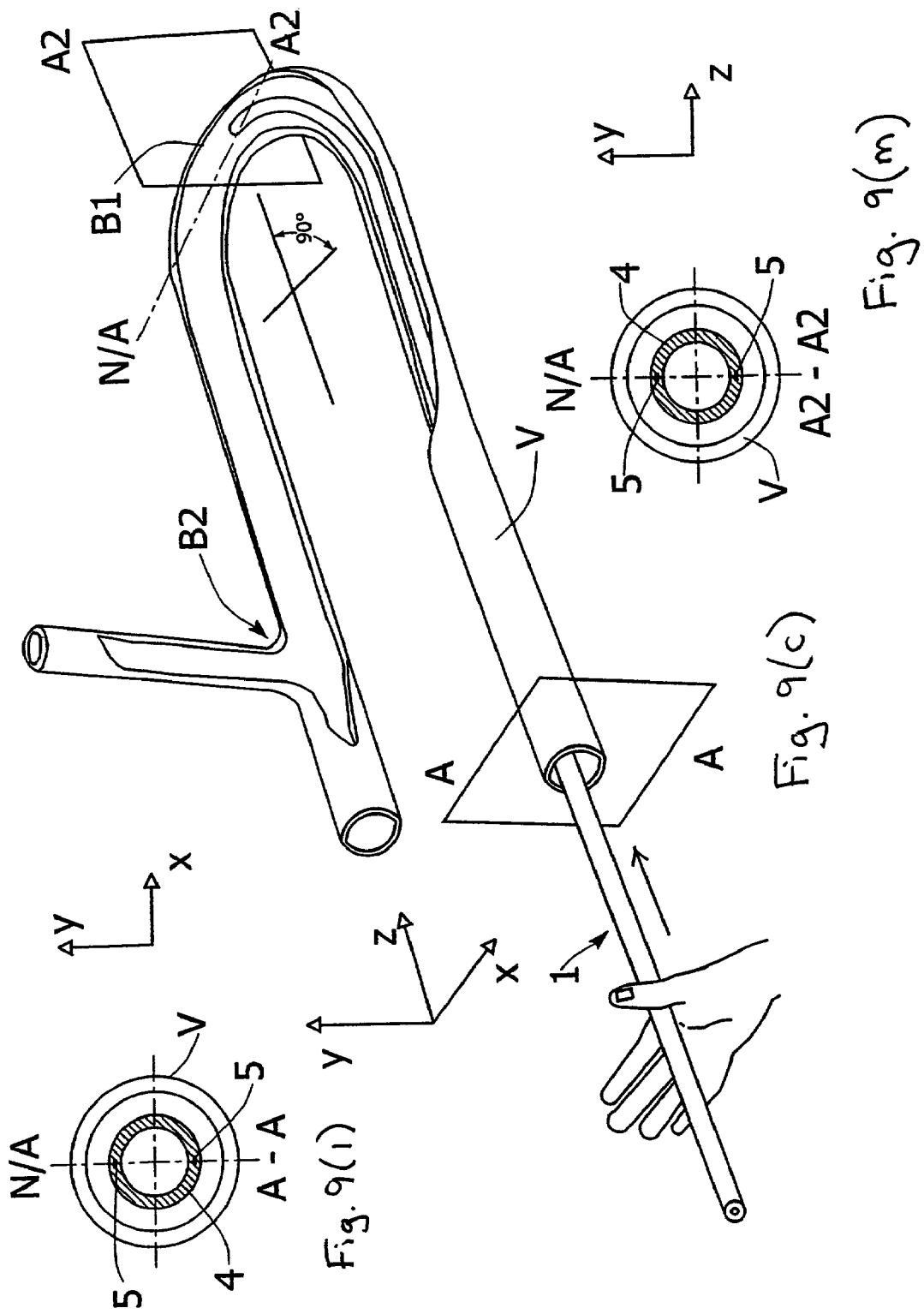

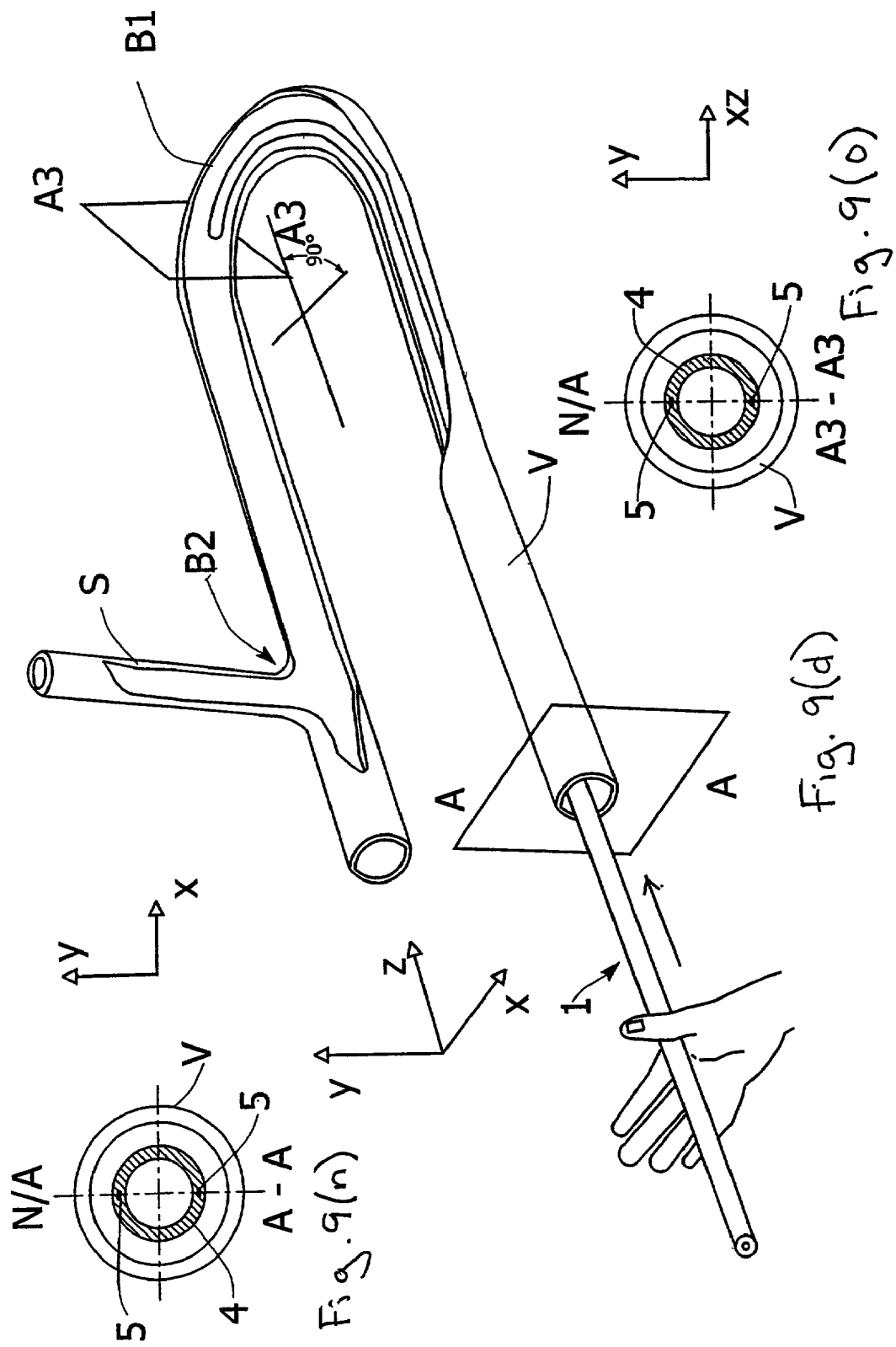

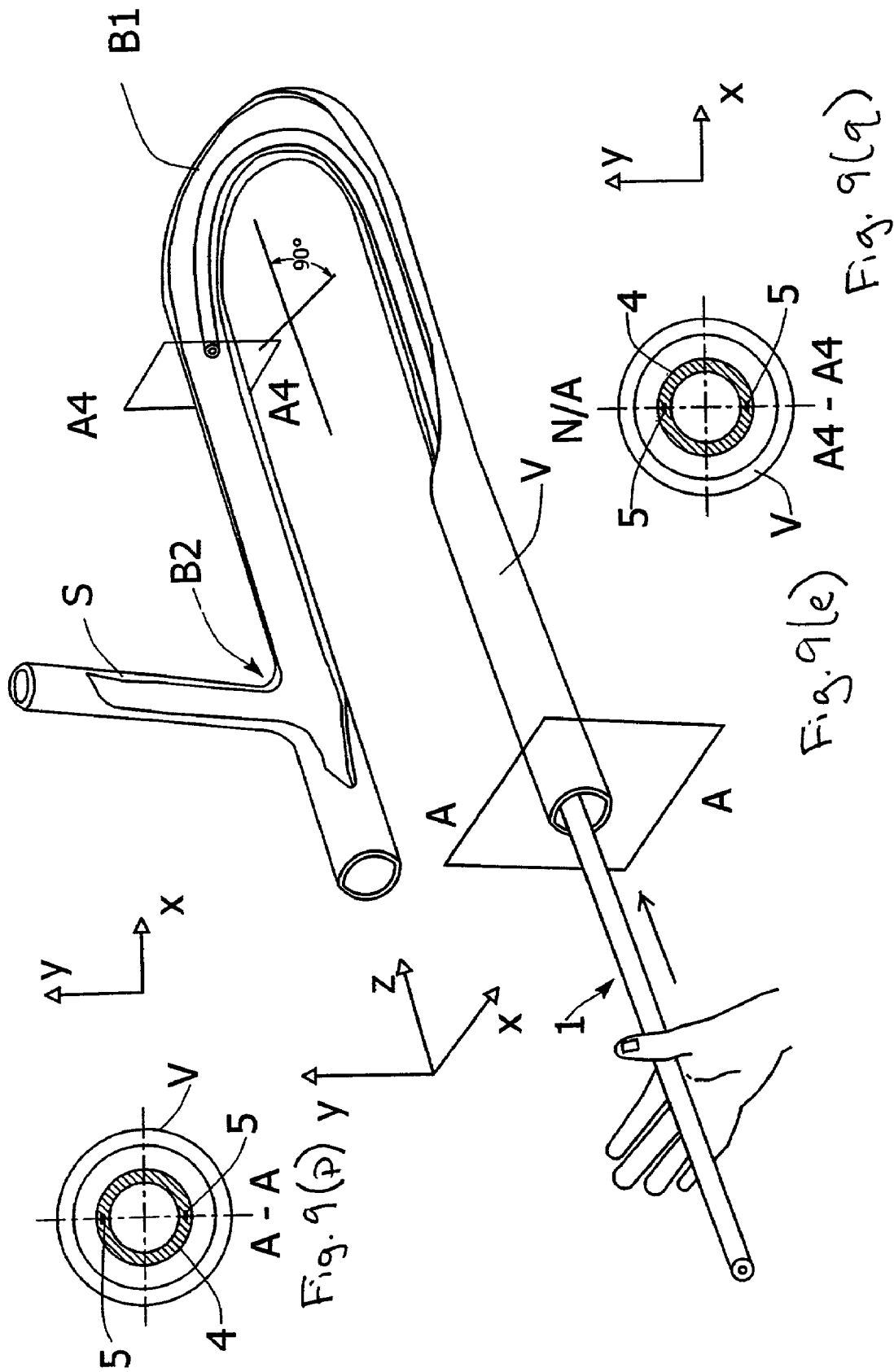

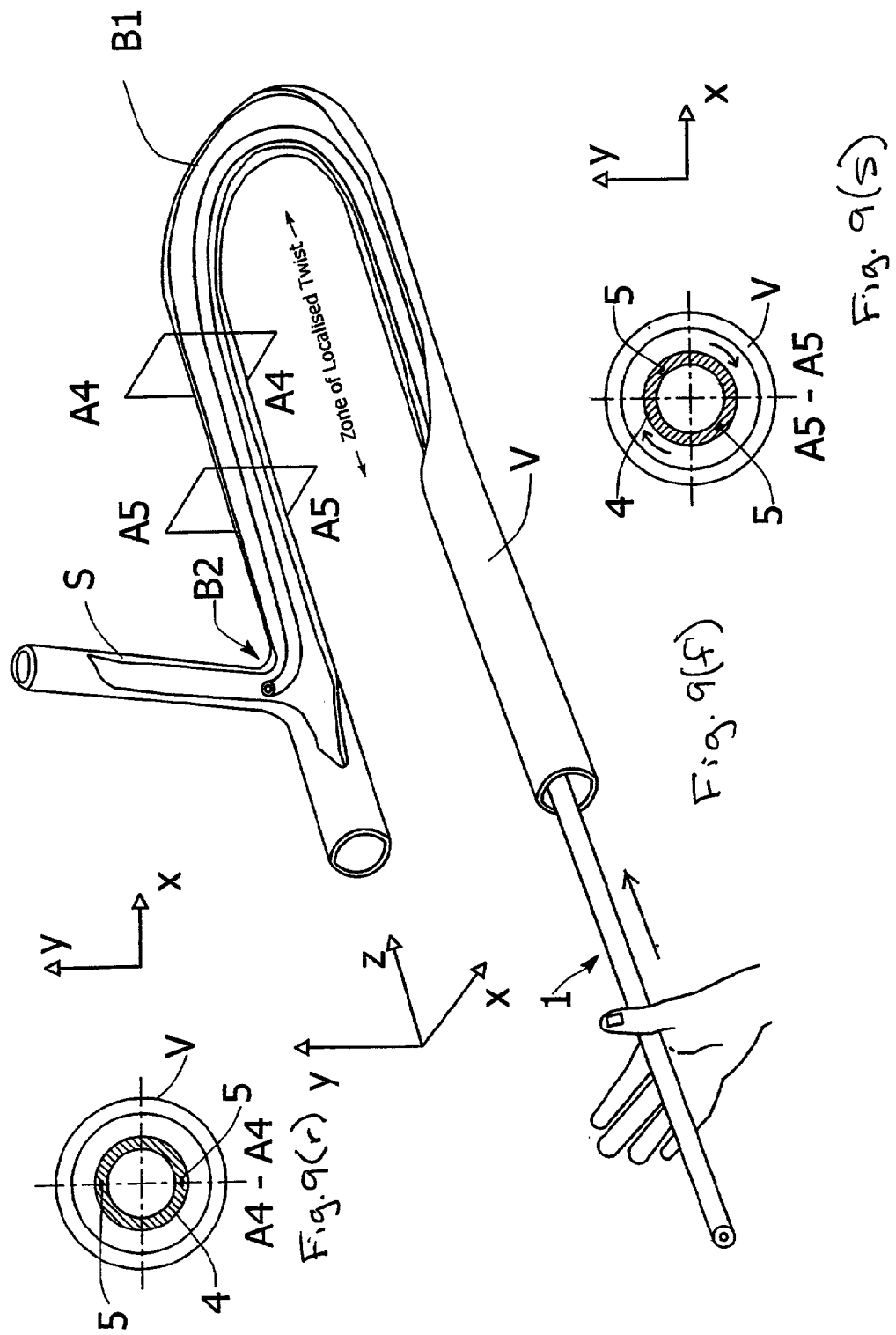

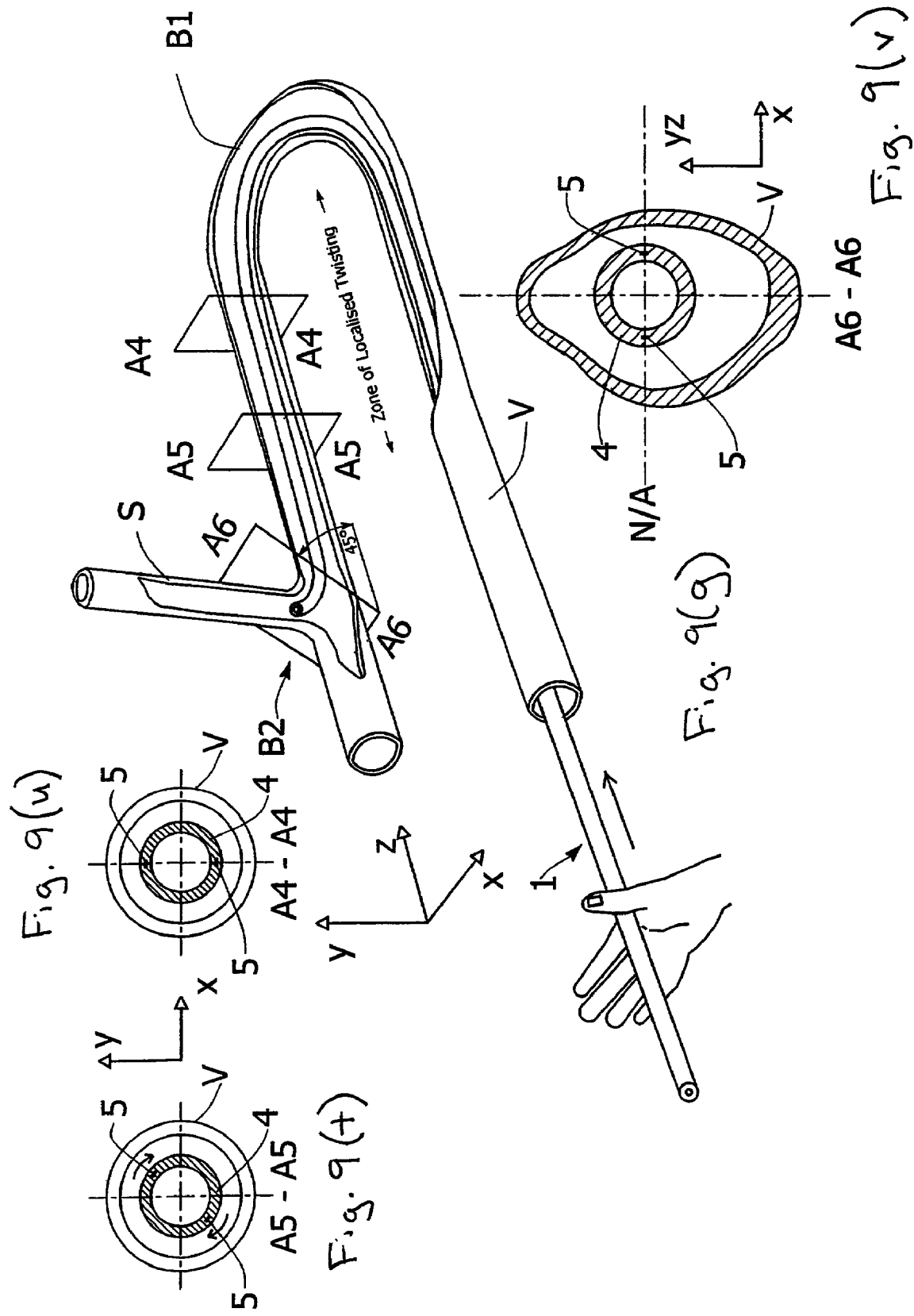

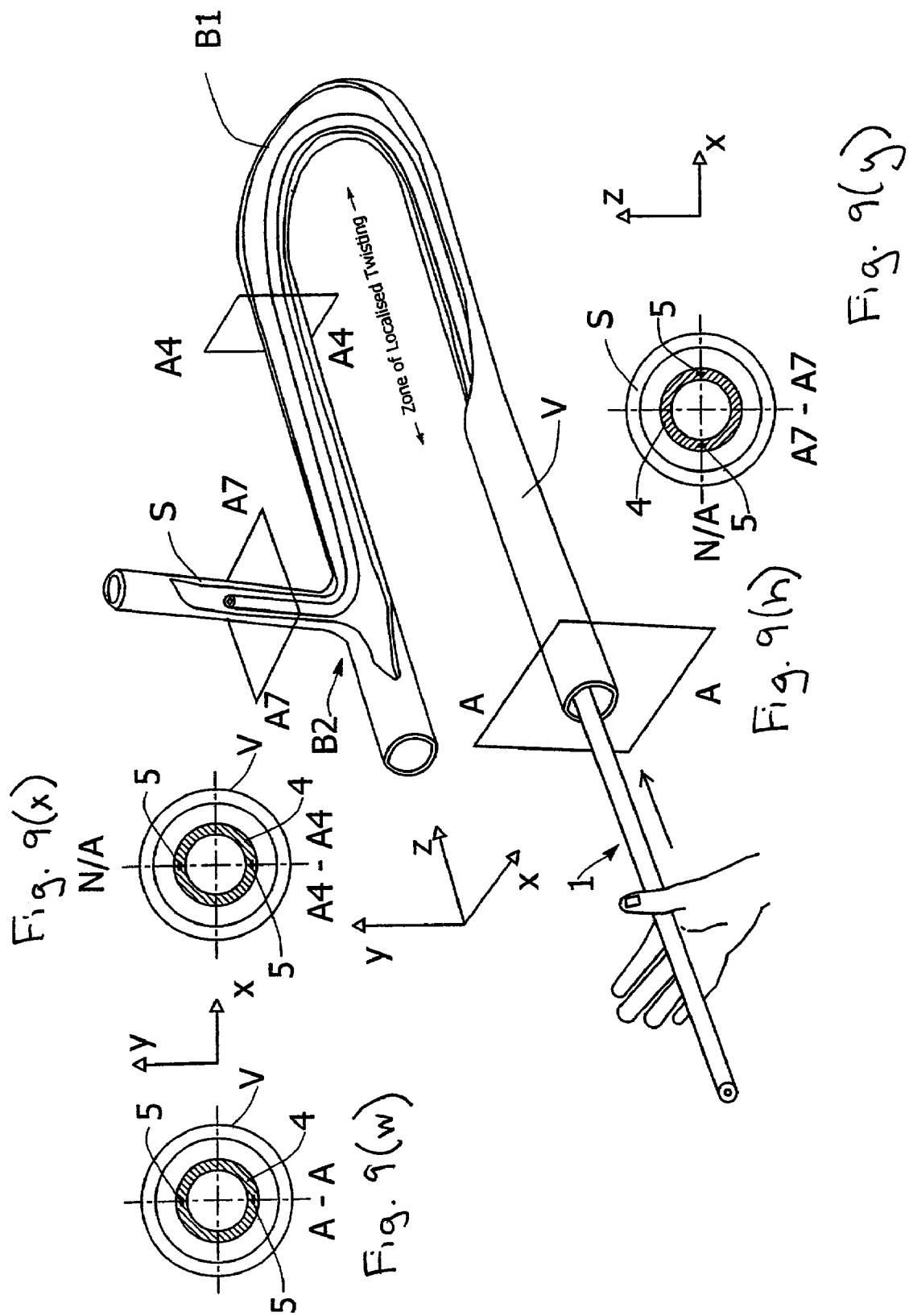

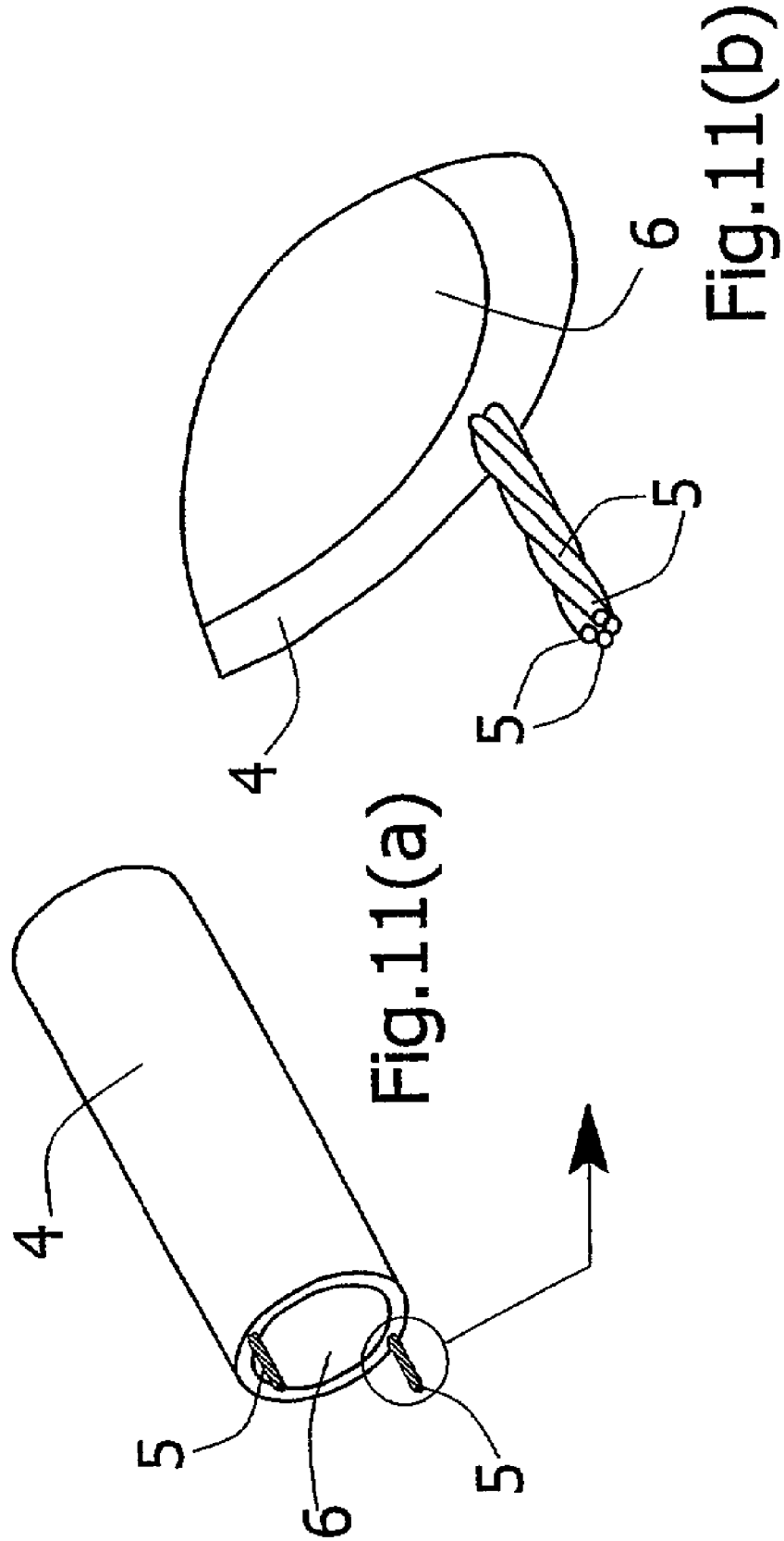

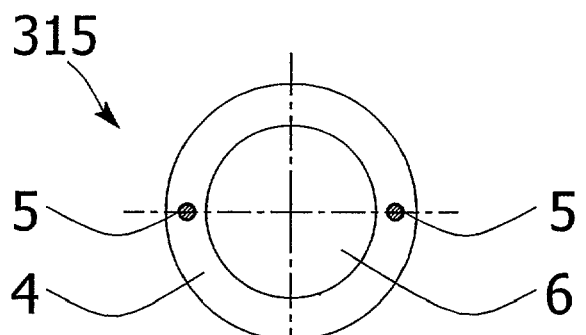
Fig.15(a)
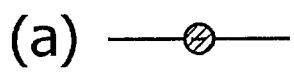
(a)
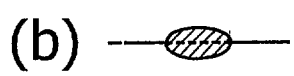
(b)
(c)
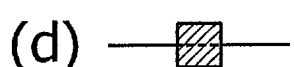
(d)
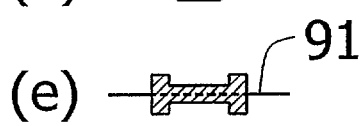
(e) 91
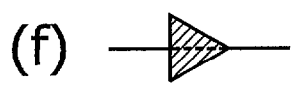
(f)
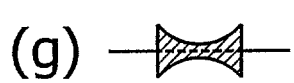
(g)
(h)
(i)
Fig.16
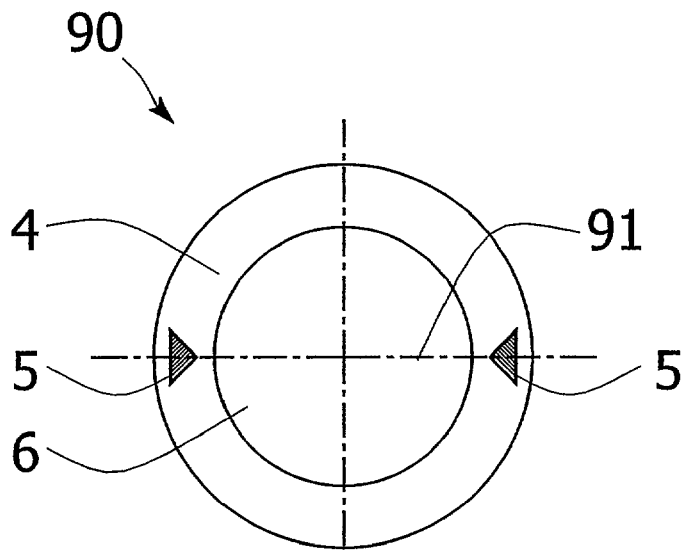
Fig.15(b)

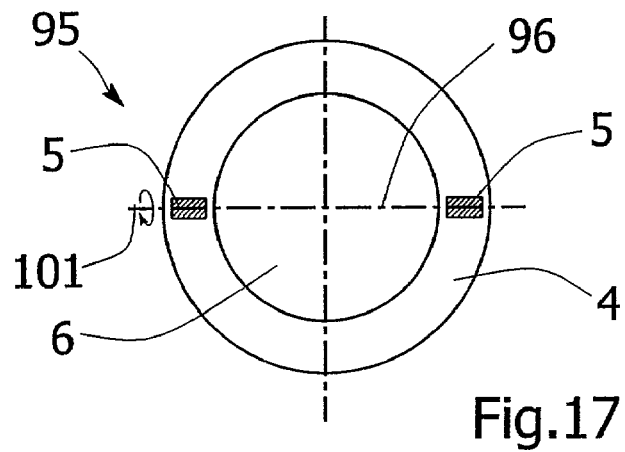
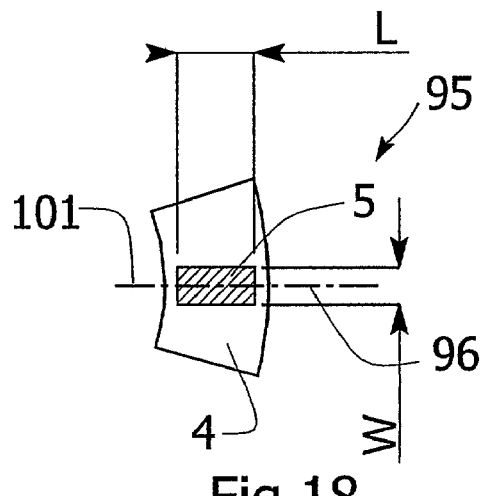
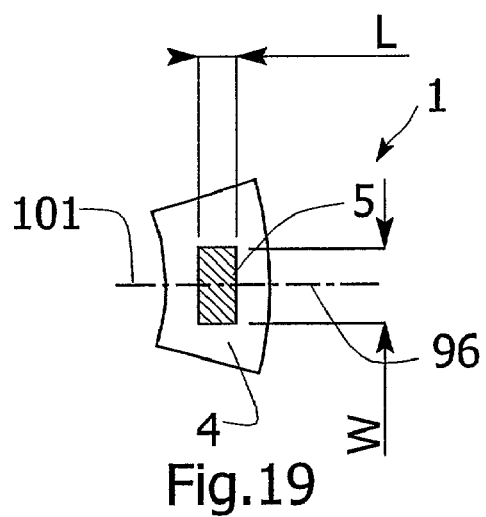

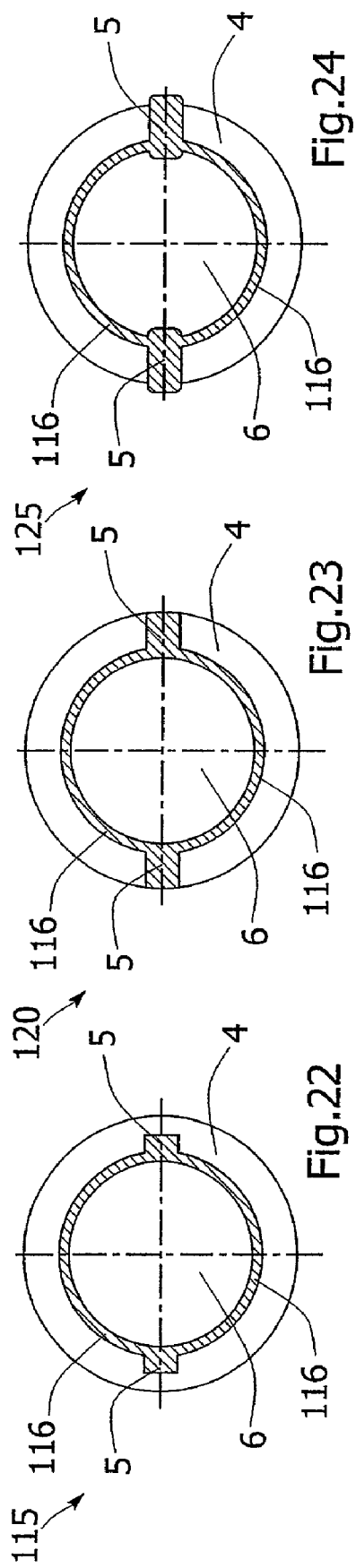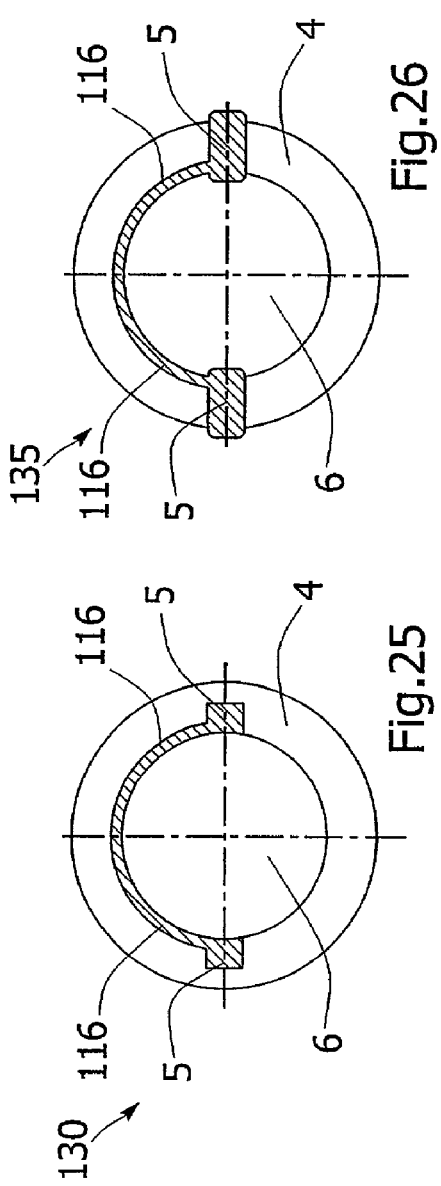

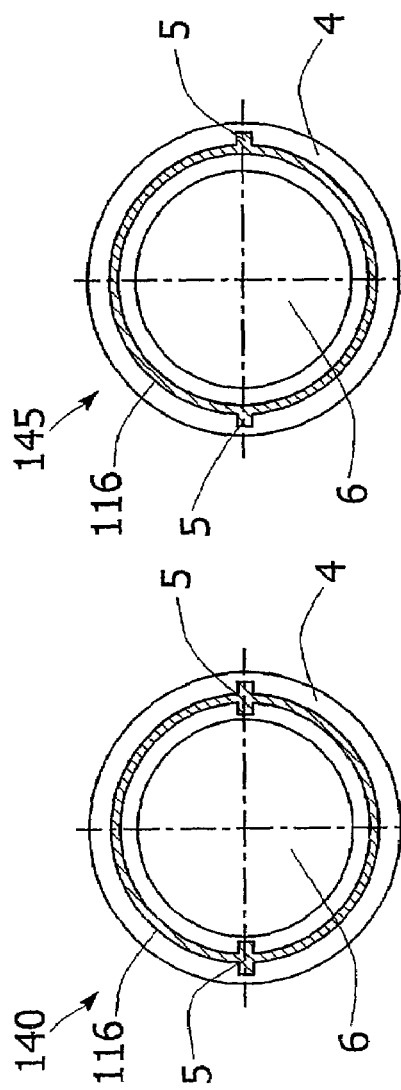
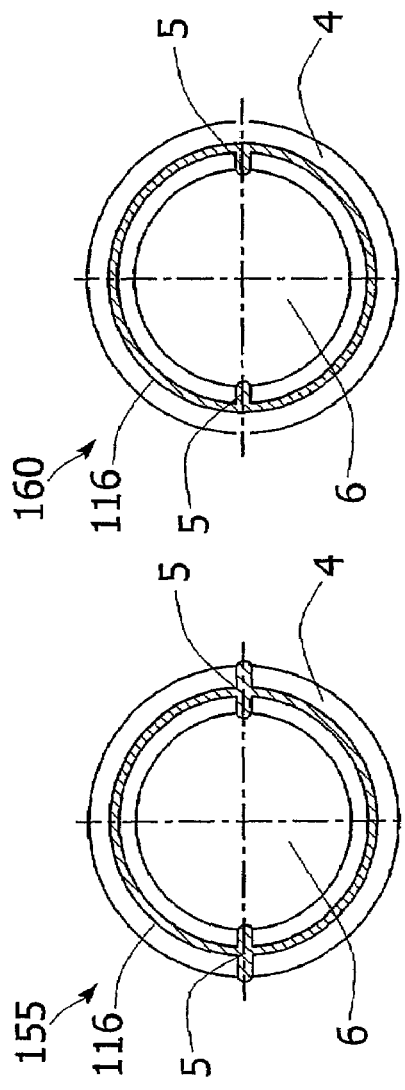
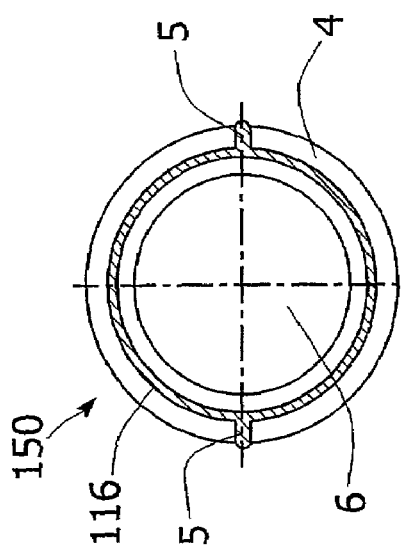
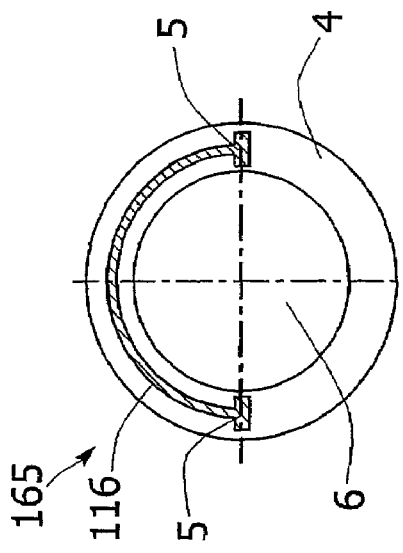

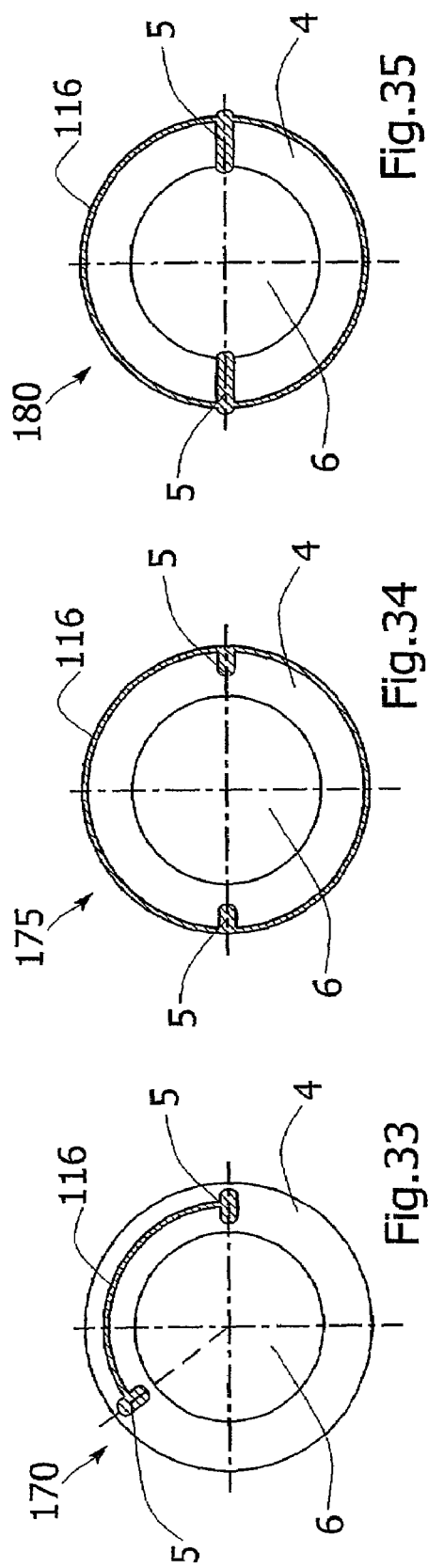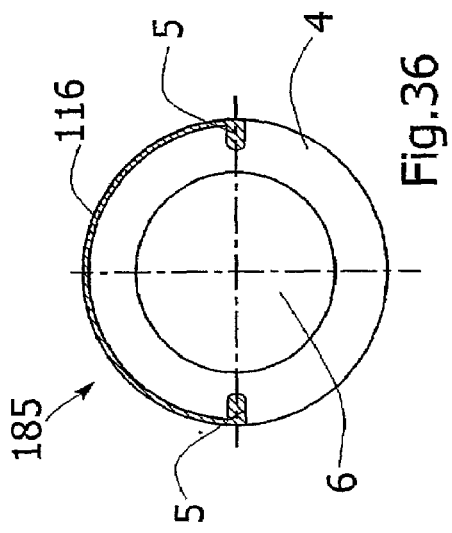

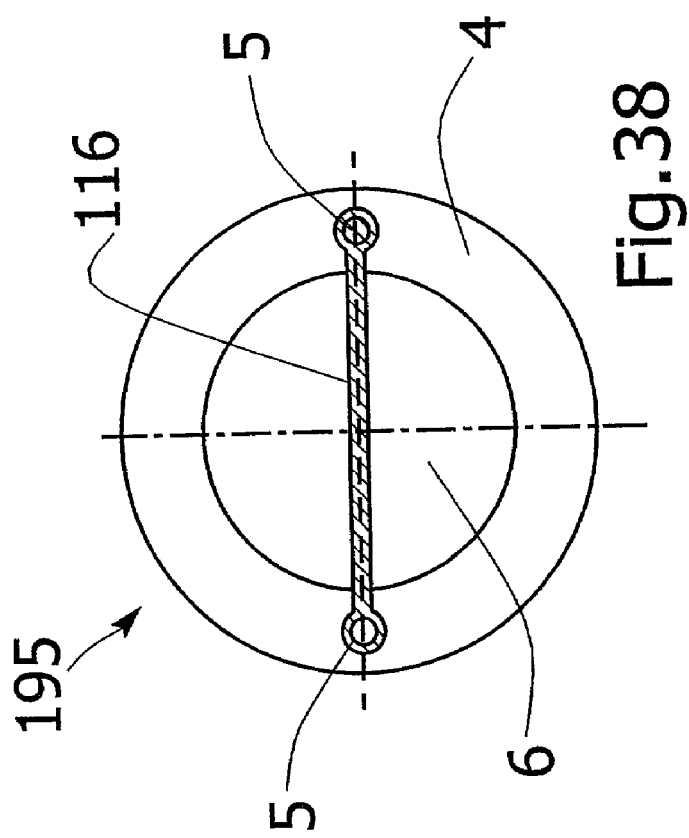
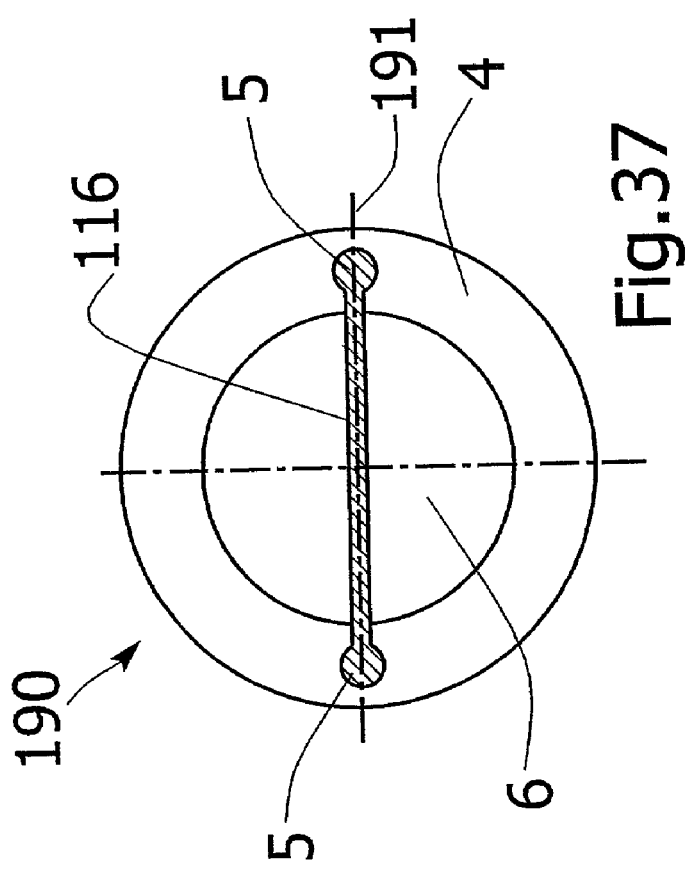

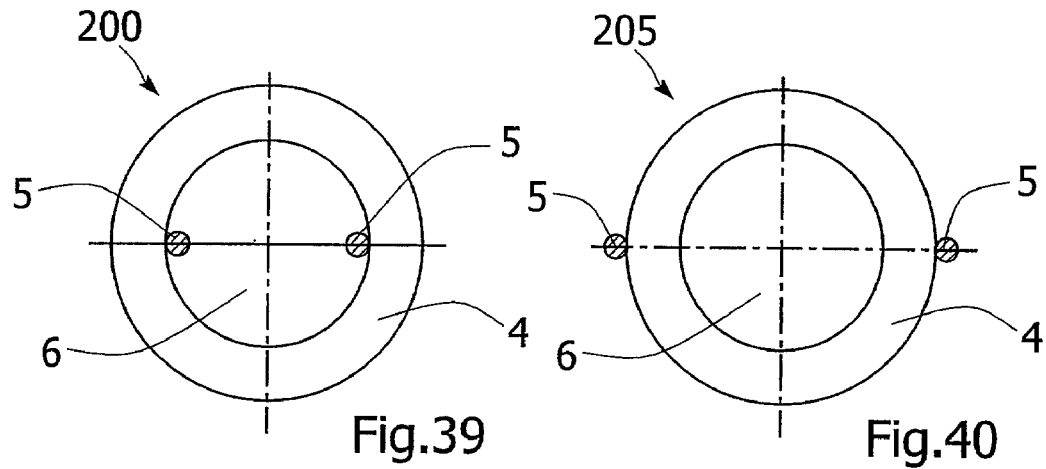
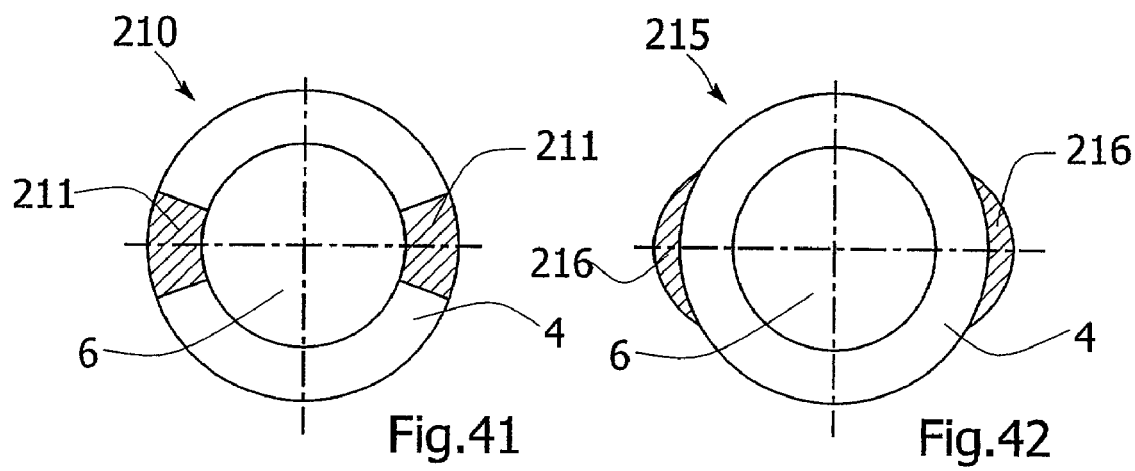
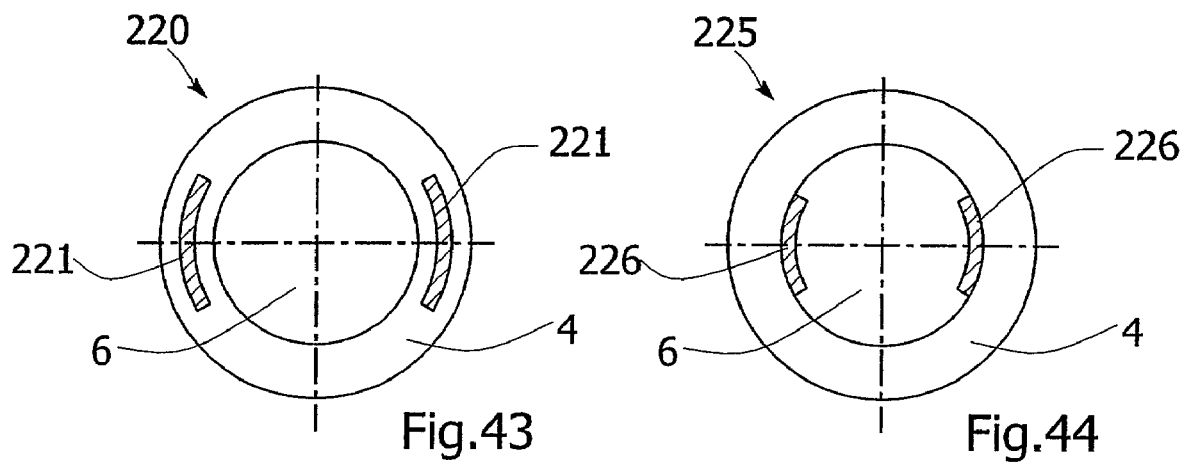

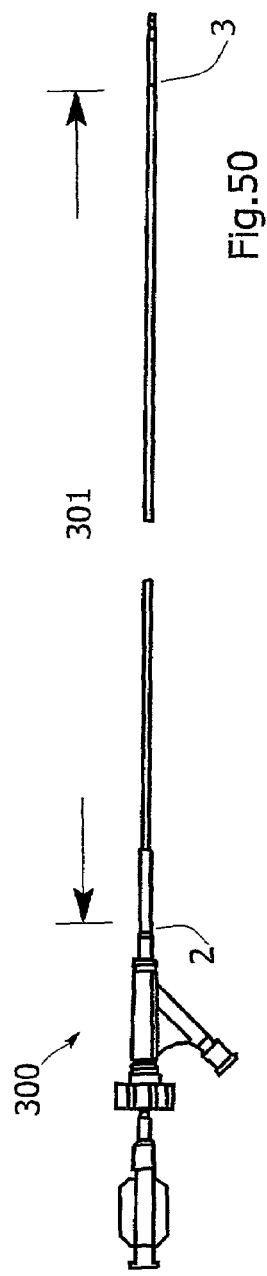
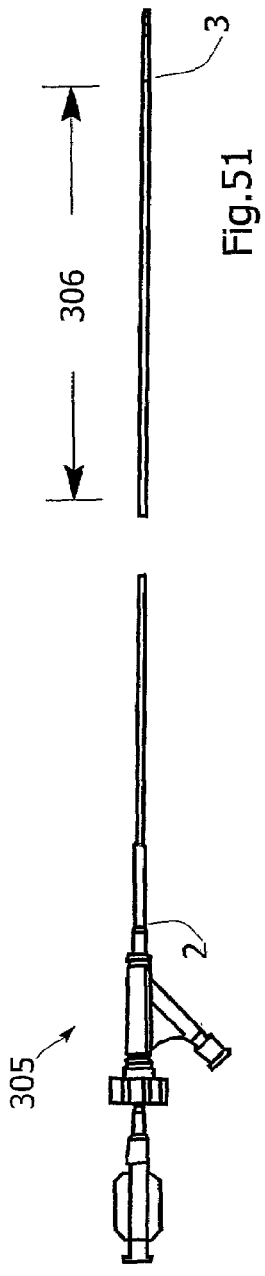
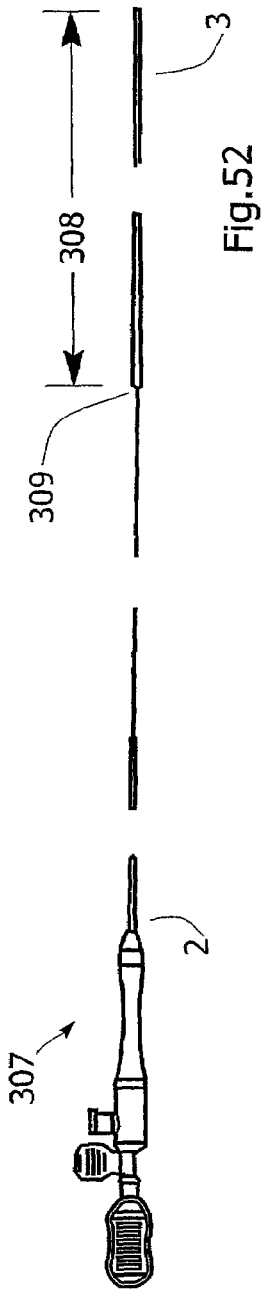

CATHETER

INTRODUCTION

This invention relates to a catheter for advancement through a body passageway of a patient.

It is known to use a catheter to deliver and/or retrieve a medical device, such as an embolic protection filter, from a location in a body passageway. Body passageways are often narrow and/or tortuous due to the natural physiology of the patient, and/or due to diseased sections of the passageway. Thus difficulty frequently arises when attempting to navigate a catheter through such a body passageway. Skill is therefore required on the part of the clinician to prevent damage being caused to the passageway and/or discomfort to the patient during advancement of a catheter.

Furthermore, the distance that the catheter distal end travels through a passageway is often very long in comparison to the cross-sectional dimensions of the catheter. Therefore a degree of pushability is essential for the catheter to be successfully advanced to the desired location in the body passageway.

Known attempts to achieve the required pushability have resulted in excessively stiff catheters which makes navigation through narrow and/or tortuous body passageways even more difficult.

This invention is therefore aimed at overcoming at least some of these problems, and in particular this invention is aimed at providing a catheter which is advancable through a body passageway.

STATEMENTS OF INVENTION

According to the invention, there is provided a catheter for advancement through a body passageway, the catheter comprising:

a flexible catheter body; and two reinforcements extending at least partially along the catheter body;

the two reinforcements being located on opposite sides of the longitudinal axis of the catheter.

The catheter of the invention has a catheter body which is sufficiently flexible so that the catheter is trackable for ease of advancement through even narrow and/or tortuous body passageways. The catheter may bend in any plane in three-dimensional space, and also may longitudinally twist during advancement through a body passageway.

The reinforcements provide the user with the necessary pushability for advancing the catheter through the body passageway, even for relatively long body passageways, while maintaining trackability.

It has been found that by locating the reinforcements on opposite sides of the longitudinal axis of the catheter, the flexible catheter body may twist during advancement through a body passageway so that the reinforcements align themselves as close to the plane of neutral bending as possible regardless of the geometry of the body passageway. In this configuration, the second moment of area of the reinforcements about the plane of neutral bending is minimised, and thus the second moment of area of the entire catheter about the plane of neutral bending is minimised. Therefore, the resistance to advancement of the catheter of the invention through a body passageway is minimised, thus resulting in a highly trackable catheter which can be successfully navigated through narrow and/or tortuous body passageways.

The invention achieves a catheter with excellent trackability characteristics combined with excellent pushability characteristics by locating two reinforcements on opposite sides of the longitudinal axis of the catheter.

The force needed to advance the catheter according to the invention is minimised. This ensures that the user enjoys excellent tactile feedback during advancement of the catheter.

A range of catheters of the invention may be provided with differing flexibilities for the catheter bodies to suit a range of passageway tortuosities.

In one embodiment of the invention, the product $(EI_{max})_R$ of the Young's modulus and the maximum second moment of area of the reinforcement is greater than the product $(EI)_m$ of the Young's modulus and the second moment of area of the catheter body material. Preferably $(EI_{max})_R$ is at least 2 times greater than $(EI)_m$. Most preferably $(EI_{max})_R$ is at least 4 times greater than $(EI)_m$. $(EI_{max})_R$ may preferably be at least 6 times greater than $(EI)_m$. Most preferably $(EI_{max})_R$ is at least 8 times greater than $(EI)_m$. Ideally $(EI_{max})_R$ is at least 10 times greater than $(EI)_m$.

In another embodiment of the invention the product $(EI_m)$ of the Young's modulus and the second moment of area of the catheter body material is greater than the product $(EI_{min})_R$ of the Young's modulus and the minimum second moment of area of the reinforcement. Preferably $(EI)_m$ is at least 10 times greater than $(EI_{min})_R$. Most preferably $(EI)_m$ is at least 50 times greater than $(EI_{min})_R$. $(EI)_m$ may preferably be at least 100 times greater than $(EI_{min})_R$. Ideally $(EI)_m$ is at least 200 times greater than $(EI_{min})_R$.

In a further embodiment the Young's modulus of the reinforcement $E_R$ is substantially greater than the Young's modulus of the catheter body material $E_m$. Preferably $E_R$ is at least 20 times greater than $E_m$. Most preferably $E_R$ is at least 100 times greater than $E_m$. Ideally $E_R$ is at least 1,000 times greater than $E_m$.

In one case a first radial line which passes through the longitudinal axis of the catheter and one reinforcement subtends an angle in the range of from 140 degrees to 180 degrees with a second radial line which passes through the longitudinal axis of the catheter and the other reinforcement. Preferably the first radial line subtends an angle in the range of from 160 degrees to 180 degrees with the second radial line. Ideally the first radial line subtends an angle of approximately 180 degrees with the second radial line.

In a preferred configuration, the reinforcements are positioned diametrically opposed on opposite sides of the longitudinal axis of the catheter. In this way, the invention provides a balanced catheter for controlled advancement of the catheter through a body passageway without the catheter veering off-centre as it is pushed distally.

The reinforcement may be fixed relative to the catheter body. Ideally the reinforcement is at least partially embedded in the catheter body. Most preferably the catheter body is oversized around the reinforcement.

The reinforcement may be provided at least partially on an external surface of the catheter body. The reinforcement may be provided at least partially on an internal surface of the catheter body.

In a preferred embodiment the catheter body is over-extruded over the reinforcements.

In one embodiment the reinforcement is of stainless steel, or nitinol, or kevlar, or carbon fibre. The reinforcement may comprise a wire. The reinforcement may comprise a spring. The reinforcement may comprise a section of hard polymeric material.

In a particularly preferred embodiment the reinforcement comprises a cluster of one or more reinforcing elements. The reinforcing elements may be interconnected. Preferably the reinforcing elements are braided together.

The reinforcing element may comprise a wire. Preferably the reinforcement comprises a cluster of two wires. Ideally the two wires are located at substantially the same radial distance from the longitudinal axis of the catheter. The two wires may preferably be radially aligned along a radial line which passes through the longitudinal axis of the catheter and both wires.

In one case the reinforcement comprises a cluster of four wires. The four wires may be clustered into a square with each wire at a corner of the square. Ideally a diagonal of the square passes through the longitudinal axis of the catheter.

The wire may be of stainless steel, or nitinol, or kevlar, or carbon fibre. The reinforcing element may comprise a spring. The reinforcing element may comprise a section of hard polymeric material.

In a preferred case one reinforcement is interconnected with the other reinforcement by a connecting arm. The connecting arm may extend at least partially circumferentially around the catheter body. The connecting arm may extend at least partially as a chord across the catheter body. Ideally the connecting arm is aligned along a line which passes through the two reinforcements.

Desirably the connecting arm extends longitudinally along the catheter.

In one embodiment the connecting arm is provided at least partially on an external surface of the catheter body. In another embodiment the connecting arm is provided at least partially on an internal surface of the catheter body.

Most preferably the connecting arm is at least partially embedded in the catheter body.

In a further embodiment of the invention the reinforcement has a generally rectangular cross-section. The reinforcement may be aligned with the long side of the rectangle substantially parallel to a radial line which passes through the longitudinal axis of the catheter and the reinforcement. The reinforcement may be aligned with the short side of the rectangle substantially parallel to a radial line which passes through the longitudinal axis of the catheter and the reinforcement.

In another embodiment the reinforcement has a generally "I" shaped cross-section. The reinforcement may be aligned with the end parts of the "I" substantially parallel to a radial line which passes through the longitudinal axis of the catheter and the reinforcement.

In a further embodiment the reinforcement has a generally round cross-section.

The reinforcement may have a generally annular cross-section.

Desirably the cross-sectional area of the reinforcement is small relative to the cross-sectional area of the catheter body.

The cross-sectional area of the reinforcement and/or of the catheter body may vary along the length of the catheter. Preferably the mechanical properties of the reinforcement and/or of the catheter body varies along the length of the catheter.

In another embodiment of the invention the catheter comprises a guide to facilitate ease of relative movement of the catheter. The guide may be provided at least partially on an external surface of the catheter. The guide may be provided at least partially on an internal surface of the catheter. Ideally the guide extends along the catheter. The guide may extend at least partially circumferentially around the catheter.

In one case the guide comprises one or more protrusions on the catheter. Preferably the protrusion is provided at least partially by the reinforcement. The protrusion may be provided at least partially by the catheter body. Most preferably the protrusion is shaped for a smooth crossing profile. In one case the guide comprises a sheath.

In a further case the catheter comprises at least one reinforcement column extending along the catheter body. The column may extend at least partially longitudinally along the catheter body. In one embodiment the column extends along the catheter body at least partially in a spiral.

In another embodiment the column is at least partially embedded in the catheter body. The column may be provided at least partially on an external surface of the catheter body. The column may be provided at least partially on an internal surface of the catheter body.

The catheter preferably comprises means to centre the catheter during advancement through a body passageway. The centring means may comprise a centring catheter for protruding distally of a distal end of the catheter. Preferably the centring catheter is retractable relative to the catheter. Most preferably the centring catheter has a tip shaped for a smooth crossing profile. Ideally the tip is arrow-head shaped, or rounded, or ball-nose shaped.

In a preferred embodiment of the invention the catheter is configured to facilitate rapid exchange of the catheter over a guidewire. Ideally the catheter comprises a guidewire lumen extending partially through the catheter from a distal end of the catheter to a rapid exchange port. The reinforcements may extend along the catheter body distally of the rapid exchange port.

Desirably the catheter comprises a hydrophilic coating.

In one embodiment of the invention the catheter is an intravascular catheter.

In another embodiment of the invention the catheter is a retrieval catheter.

In a further embodiment of the invention the catheter is a delivery catheter.

In a further aspect of the invention there is provided a method for performing a procedure in a body passageway comprising the steps of:
  providing a catheter having a flexible catheter body and a reinforcement extending along the catheter body;
  introducing the catheter into the body passageway;
  advancing the catheter through the body passageway to a location of tortuosity;
  pushing the catheter axially, the catheter twisting spontaneously to follow the contour of the tortuosity, on pushing.

In one embodiment the location of tortuosity is a bend in two dimensions and the catheter is substantially uniformly angularly displaced spontaneously around the bend, on pushing of the catheter.

In another embodiment the location of tortuosity is a bend in three dimensions and the catheter twists spontaneously in the local area of the tortuosity, on pushing of the catheter.

Preferably the procedure is an intravascular procedure and the catheter is introduced into the vasculature.

In one case the catheter is a delivery catheter and the method comprises the step of:
  delivering a medical or therapeutic device or material to a location distal of the location of tortuosity.

In another case the catheter is a retrieval catheter and the method comprises the step of:
  retrieving a medical or therapeutic device or material from a location distal of the location of tortuosity.

In a particularly preferred embodiment the medical device is an embolic protection filter.

The two reinforcements preferably have high tensile and compressive strengths to ensure that the catheter is pushable during advancement through a body passageway.

In a preferred arrangement the shape of the reinforcement may be configured to minimise the width of material perpendicular to the diameter running through the centre of the reinforcement. These shapes may however prove difficult to manufacture.

BRIEF DESCRIPTION OF THE DRAWINGS

The invention will be more clearly understood from the following description of some embodiments thereof, given by way of example only, with reference to the accompanying drawings, in which:

FIGS. 9(a) to 9(y) are views of a catheter according to the invention being moved through a body passageway;

FIG. 11(a) is a perspective view of another catheter according to the invention;

FIG. 11(b) is an enlarged view of part of the catheter of FIG. 11(a);

FIGS. 12 to 15(b) are end views of other catheters according to the invention;

FIGS. 16(a) to 16(i) are end views of other reinforcements;

FIG. 17 is an end view of another catheter according to the invention;

FIG. 18 is an enlarged view of part of the catheter of FIG. 17;

FIG. 19 is an enlarged view of part of the catheter of FIG. 2;

FIGS. 22 to 44 are end views of further catheters according to the invention;

FIGS. 50 to 52 are side views of other catheters according to the invention.

DETAILED DESCRIPTION

Figure 1:
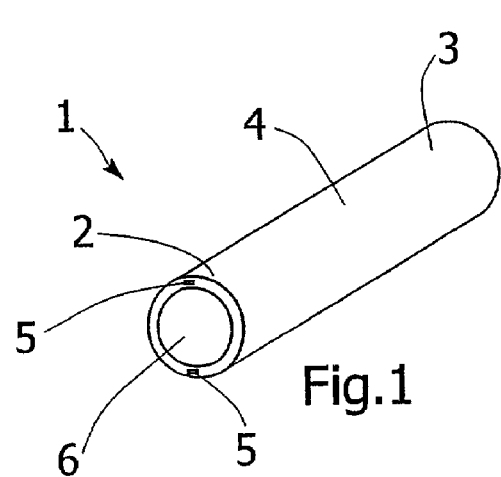
FIG. 1 is a perspective view of a catheter according to the invention.

Referring to the drawings and initially to FIGS. 1 to 7 thereof, there is illustrated a catheter 1 according to the invention suitable for advancement through a body passageway of a patient.

The catheter 1 has a longitudinal axis, extends between a proximal end 2 and a distal end 3, and defines an inner lumen 6.

The catheter 1 comprises a catheter body 4 which is flexible to provide the necessary trackability for the catheter 1 to advance through a body passageway, and two reinforcements 5 extending along the catheter body 4 which provide the necessary pushability to advance the catheter 1 through the passageway.

The reinforcements 5 are fixed relative to the catheter body 4. In this case, the catheter body 4 is over-extruded over the reinforcements 5 to form the catheter 1, the reinforcements 5 being completely embedded within the catheter body 4 during the over-extrusion process for secure fixing of the reinforcements 5 within the catheter body 4 (FIG. 2(a)).

Figure 2:
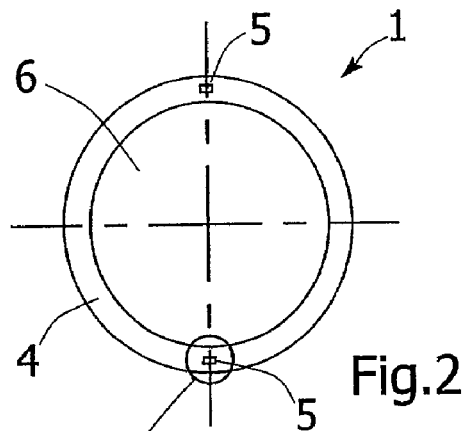
FIG. 2 is an end view of the catheter of FIG. 1.
Figure 2A:
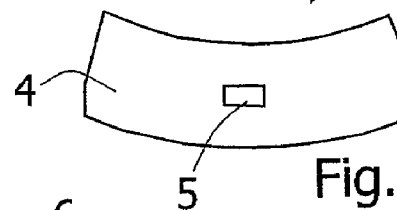
FIG. 2(a) is an enlarged view of part of the catheter of FIG. 2.

The reinforcements 5 are positioned opposed to one another, in this case by approximately 180 degrees, on opposite sides of the longitudinal axis of the catheter 1 (FIG. 2).

The reinforcements 5 are each provided, in this case, by a narrow wire of rectangular cross-section extending along the length of the catheter body 4. The reinforcement wires 5 are of a stiff material, such as stainless steel. By ensuring that the wire cross-sectional area is small relative to the catheter body cross-sectional area, the resistance to the trackability of the catheter 1 due to the stiff wires 5 is minimised.

The catheter body 4 is relatively soft and twistable. This enables the entire catheter 1 to twist during advancement so that the reinforcements 5 will substantially orientate themselves along a plane of neutral bending during advancement of the catheter 1. In this way, any resistance to the trackability of the catheter 1 due to the stiff reinforcements 5 is minimised.

Figure 6:
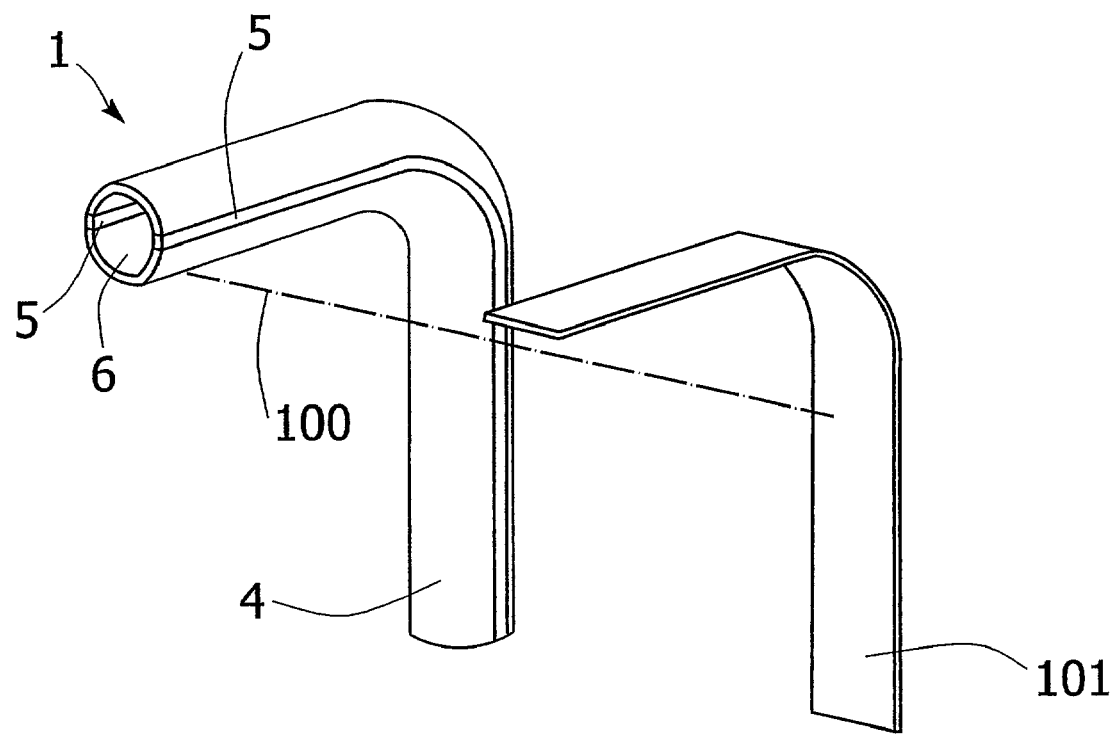
FIG. 6 is a schematic illustration of the catheter of FIG. 1 in use.

The plane of neutral bending is defined as a plane running through the catheter 1 where the catheter material is neither in tension nor in compression. Referring to FIG. 6, there is illustrated a portion of the catheter 1 bent around an axis of bending 100. If a cross-section of the catheter 1 on the bend 100 is examined, the neutral axis is seen to run approximately through the centre of the cross-section along a diameter, parallel to the axis of bending 100, and is the axis where material is neither in tension nor in compression. A plane of neutral bending 101 is illustrated schematically on the right hand side in FIG. 6. The plane of neutral bending 101 contains the neutral axis of every cross section along the length of the catheter 1. This plane 101 is a complex three-dimensional surface which may twist in a number of directions depending on the passageway tortuousity.

Figure 7:
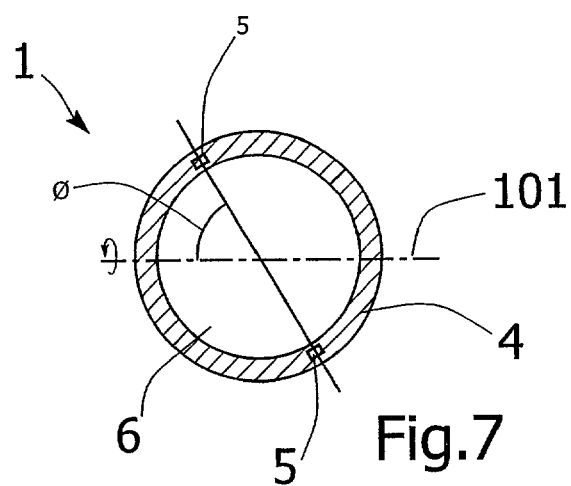
FIG. 7 is an end view of the catheter of FIG. 1.
Figure 7A:
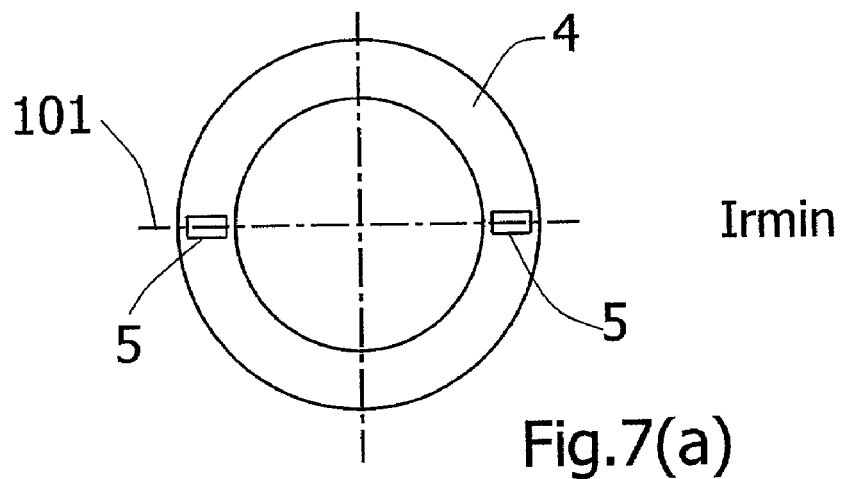
FIGS. 7(a), 7(b) and 7(c) are cross sectional views of various catheters of the invention.
Figure 7B:
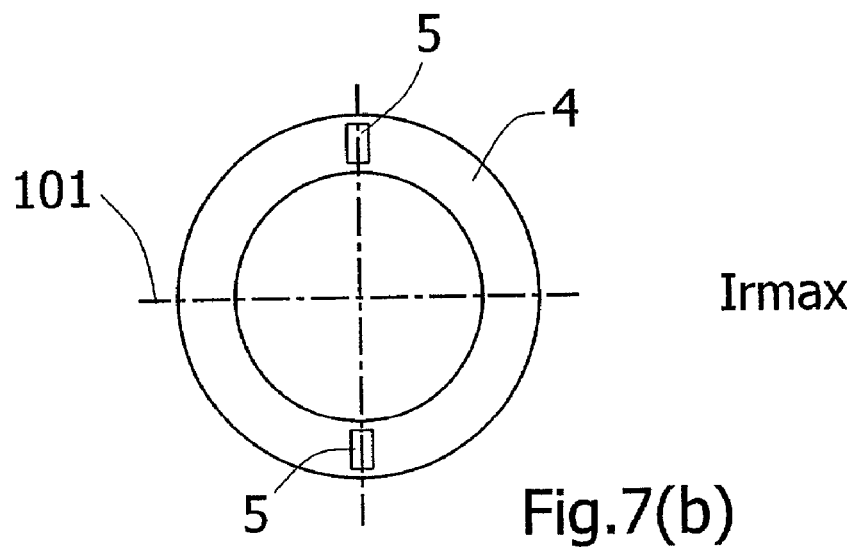
Figure 8:
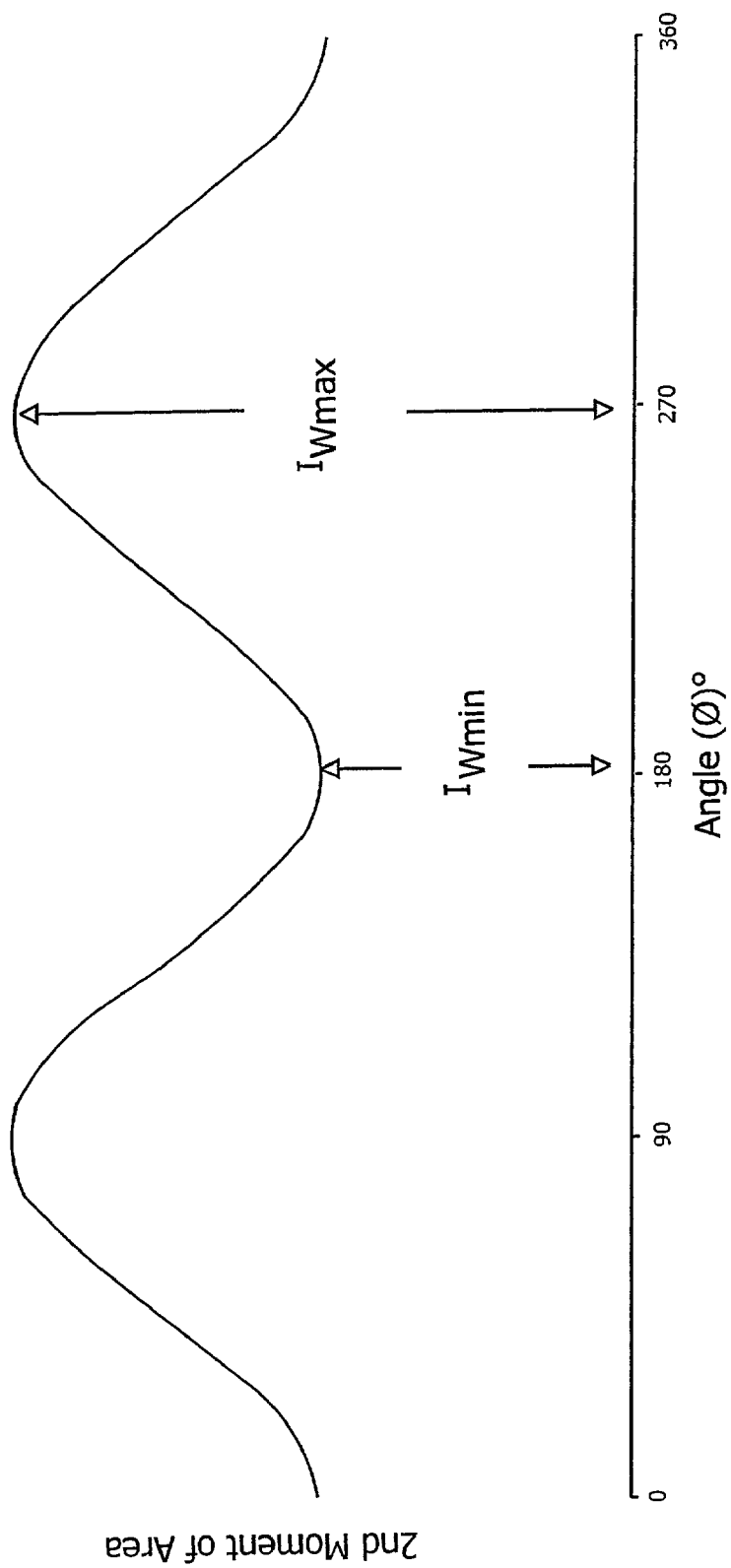
FIG. 8 is a graph illustrating the variation of the angle (θ) between a reinforcement of the catheter of FIG. 1 and the neutral axis with the second moment of area of the reinforcement around the neutral axis.

FIGS. 7 and 8 illustrate the variation of second moment of area of the reinforcements 5 around the neutral axis 101 as the angular displacement (θ) between the reinforcements 5 and the neutral axis 101 is varied. The resistance to advancement of the catheter 1 through a tortuous path is minimised when the reinforcements 5 are aligned along the neutral axis 101 because the second moment of area of the reinforcements 5, and hence of the entire catheter 1, around the neutral axis 101 is minimised. Therefore the force required to bend the catheter 1 is also minimised. This ensures that the catheter 1 is sufficiently trackable to navigate through a potentially narrow and/or tortuous passageway with minimal resistance.

It will be appreciated that the graph illustrated in FIG. 8 is schematic. All catheter constructions will not replicate this graph shape exactly. However, in general the graph will have peaks and troughs, similar to those illustrated in FIG. 8.

By positioning the reinforcements 5 symmetrically opposing one another along each side of the catheter body 4, this ensures that the catheter 1 is balanced, and thus there will be no veering of the catheter 1 off-centre during advancement.

We have observed two phenomena with the catheters of this invention. Firstly, when the catheter is advanced through simple 2D bends the catheter shafts spontaneously orient themselves such that the reinforcements lie as close to the neutral axis as possible. This involves a uniform angular displacement of the catheter into the low energy configuration. In this scenario we have found that there is no angular displacement of one catheter segment relative to another plane. The entire catheter turns.

Secondly, when the catheter is advanced through complex and tortuous bends the catheter shaft spontaneously twists in the area local to the bends. In this situation there may be significant angular displacement of one catheter segment relative to the next. We have found that this twisting is concentrated in the area of tortuosity.

We have found that the relationship between the bending stiffness parameters (EI) of the reinforcement and of the matrix material is important in providing catheters which will perform in this way. The product $EI_{max}$ for the reinforcement must be much greater than the product EI for the matrix component. EI of the matrix is substantially greater than $EI_{min}$ of the reinforcement. This means that the catheter shaft is reinforced without effecting the bending stiffness of the shaft. The second moment of area contribution of the reinforcement about the neutral axis of the catheter must vary strongly as a function of angular orientation i.e. $I_{max} \gg I_{min}$. The Young's modulus (E) of the reinforcement must be very much larger than that of the matrix. In referring to Young's modulus of the matrix material it will be appreciated that with polymeric materials the modulus varies as a function of strain. In general for polymeric matrices the apparent modulus is less than Young's modulus.

FIG. 7(*a*) illustrates a catheter configuration in which the reinforcements 5 are co-axial with the plane 101 of neutral bending of the catheter. In this configuration the second moment of area of the reinforcement about the neutral axis ($I_{Rmin}$) is minimised. In the configuration of FIG. 7(*b*) angular displacement between the reinforcements 5 and the plane of neutral bending is maximised. In this configuration the second moment of area of the reinforcement about the neutral axis ($I_{Rmax}$) is maximised.

FIG. 7(*c*) illustrates a catheter configuration similar to FIG. 7(*a*) in which the reinforcements 5 are arranged so that the short side of the rectangle is substantially parallel with the neutral axis and the long side is at right angles to the neutral axis.

A typical catheter of FIG. 7(*c*) according to the invention has the following details:

Matrix Material (4): Pellethane 2363-65D (Polyurethane Elastomer.)
Modulus: 0.221 GPa
Dimensions:
Tube OD: 1.8 mm
Tube ID: 0.4 mm Reinforcement Material (5): Stainless Steel
Modulus: 210 GPa
Dimensions (Flat Wire):
Width: 0.038 mm
Height: 0.076 mm
Orientation:
$I_{Rmax}$ ($2^{nd}$ Moment of Area contribution of the two wires to the catheter shaft about the neutral axis)=$3.69 \times 10^{-3}$ mm$^4$
$I_{Rmin}$ ($2^{nd}$ Moment of Area contribution of the two wires to the catheter shaft about the neutral axis)=$2.78 \times 10^{-6}$ mm$^4$
$\Delta I = I_{Rmax} - I_{Rmin}$
$\Delta I = 3.68 \times 10^{-3}$ mm$^4$
$\Delta I$ is a significant component in driving the spontaneous twisting effect.
$I_{Matrix}$ ($2^{nd}$ Moment of Area contribution of the matrix to the catheter shaft about the neutral axis)=0.323 mm$^4$
Now where E=Modulus of respective materials
$EI_{Rmax}$=0.7749 GPa.mm$^4$
$EI_{Rmin}$=$5.8 \times 10^{-4}$ GPa.mm$^4$
$EI_{Matrix}$=0.07138 GPa.mm$^4$
$EI_{max}$ of the reinforcement is therefore greater than EI of the matrix.
EI of the matrix is substantially greater than $EI_{min}$ of the reinforcement.
Similar calculations can be made for other matrix materials using the following tables for Young's modulus:

| Matrix Materials | |
| --- | --- |
| Material | Modulus (E) |
| Pellethane 2363-65D (Polyurethane) | 0.221 GPa |
| Pebax 6333 (Polyether Block Amide) | 0.307 GPa |
| Nylon 11 (Polyamide) | 0.61 GPa |
| Polyimide | 4 GPa |

Similar calculations can also be made for other reinforcement materials using the following table for Young's modulus:

| Matrix Materials | |
| --- | --- |
| Material | Modulus (E) |
| Stainless Steel | 200 GPa |
| Nitinol (NiTi Shape Memory Alloy) | 75 GPa |
| Kevlar 49 (Aramid Fibre) | 112 GPa |
| Hexcel Carbon Fibre | 228 GPa |

Changing the orientation of the reinforcement to that of FIG. 7(*a*) provides the following:
$I_{Rmax}$ ($2^{nd}$ Moment of Area contribution of the two wires to the catheter shaft about the neutral axis)=$3.69 \times 10^{-3}$ mm$^4$
$I_{Rmin}$ ($2^{nd}$ Moment of Area contribution of the two wires to the catheter shaft about the neutral axis)=$6.95 \times 10^{-7}$ mm$^4$
$I_{Matrix}$ ($2^{nd}$ Moment of Area contribution of the matrix to the catheter shaft about the neutral axis)=0.323 mm$^4$
Now where E=Modulus of respective materials
$EI_{Rmax}$=0.7768 GPa.mm$^4$
$EI_{Rmin}$=$1.45 \times 10^{-4}$ GPa.mm$^4$
$EI_{Matrix}$=0.07138 GPa.mm$^4$
$EI_{max}$ of the reinforcement is therefore greater than EI of the matrix.
EI of the matrix is substantially greater than $EI_{min}$ of the reinforcement.

Changing the profile of the reinforcement to a round wire Dia.=0.06 mm and using the same tube dimensions gives the following:

$I_{Rmax}$ ($2^{nd}$ Moment of Area contribution of the two wires to the catheter shaft about the neutral axis)=$3.62 \times 10^{-1}$ mm$^4$ $I_{Rmin}$ ($2^{nd}$ Moment of Area contribution of the two wires to the catheter shaft about the neutral axis)=$1.27 \times 10^{-6}$ mm$^4$ $I_{Matrix}$ ($2^{nd}$ Moment of Area contribution of the matrix to the catheter shaft about the neutral axis)=0.3122 mm$^4$ Now where E=Modulus of respective materials $EI_{Rmax}$=0.7602 GPa.mm$^4$
$EI_{Rmin}$=$2.67 \times 10^{-4}$ GPa.mm$^4$
$EI_{Matrix}$=0.06900 GPa.mm$^4$ $EI_{max}$ of the reinforcement is therefore greater than EI of the matrix.

EI of the matrix is substantially greater than $EI_{min}$ of the reinforcement.

We have found that the potential for spontaneous twisting to occur as described above within the catheter shaft is substantial if the catheter exhibits the characteristic that $(EI_{max})_R$ is greater than, preferably much greater than $(EI)_m$. $(EI)_m$ should also be greater than, preferably much greater than $(EI_{min})_R$. This means that the catheter shaft is reinforced with minimal impact on the bending stiffness.

The catheter body 4 is of a generally flexible material which may be selected from the polyurethane group of materials, in this case the catheter body material is Pellethane. Alternatively the catheter body 4 may be selected from the peba group of materials, such as Pebax. Pellethane is a TradeMark of Dow Chemical, and Pebax is a TradeMark of Elf Atochem. Alternatively the catheter body 4 may be selected from the fluoropolymer group of materials, for example a polytetrafluoroethylene. Alternatively the catheter body 4 may be selected from the polyester group of materials. Further alternative materials for the catheter body 4 are silicons, polyethylenes, nylons, polyolefins, polyimides, and elastomers, or a blend of two or more of any of the above mentioned materials.

Preferably the catheter body material has a modulus of less than 5, for example less than 2, and most preferably less than 0.5 GPa.

The reinforcements 5 preferably have a high tensile strength, and/or a high compressive strength, and/or a high modulus of elasticity and/or a high compressibility modulus of elasticity. Examples of suitable reinforcements include Kevlar (TradeMark) strands, spring (especially tight coiled spring), or metallic, especially stainless steel wire. Stainless steel is particularly suitable because of the high modulus that it achieves for a relatively small cross-sectional area.

Preferably the reinforcement has a modulus of greater than 50, for example greater than 100, most preferably greater than 200 GPa.

In use, the catheter 1 is introduced into a body passageway and advanced through the passageway. The catheter body 4 is flexible so that as the catheter 1 is advanced through the passageway, the catheter 1 may twist and bend to facilitate passage of the catheter 1 through the potentially tortuous passageway, as illustrated in FIG. 3.

The catheter body 4 is longitudinally twistable during advancement of the catheter 1. This enables a portion of the catheter 1 to twist so that the reinforcements 5 are orientated along the plane of neutral bending 101 at each bend in the passageway, thus minimising the resistance to advancement of the catheter 1 through the passageway.

Figure 3:
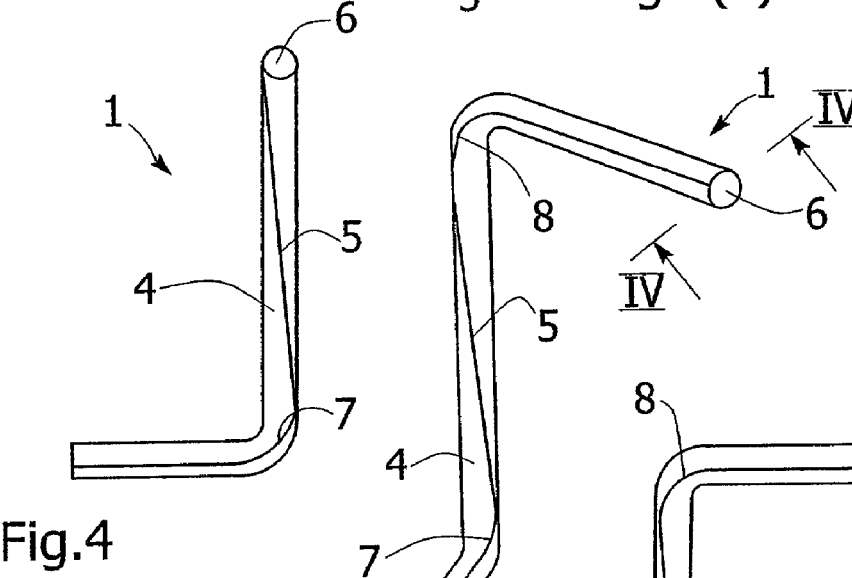
FIG. 3 is a perspective view of the catheter of FIG. 1 in use.
Figure 4:
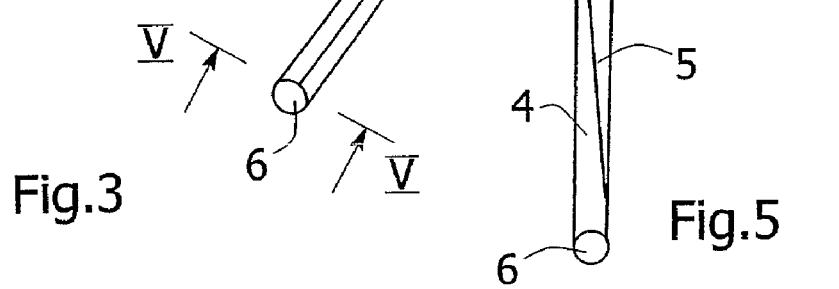
FIG. 4 is a view along line IV—IV in FIG. 3.
Figure 5:
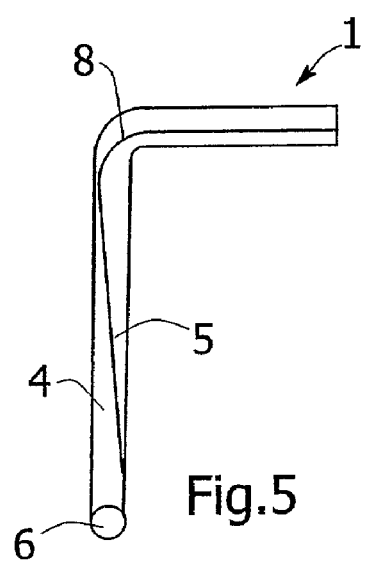
FIG. 5 is a view along line V—V in FIG. 3.

FIG. 3 illustrates the reinforcements 5 positioned along the plane of neutral bending 101 at a first bend 7 in the catheter 1 corresponding to a bend in the passageway, and the reinforcements 5 positioned along the plane of neutral bending 101 at a second bend 8 in the catheter 1 corresponding to another bend in the passageway. In this case, the second bend 8 is substantially perpendicular to the first bend 7. Between the first bend 7 and the second bend 8, the catheter body 4 and the reinforcements 5 twist, as illustrated, to ensure that the reinforcements 5 are positioned along the plane of neutral bending 101 at both of the bends 7, 8. Thus the resistance to bending of the catheter 1 at each bend 7, 8 due to the presence of the reinforcements 5 is minimised.

Figure 7C:
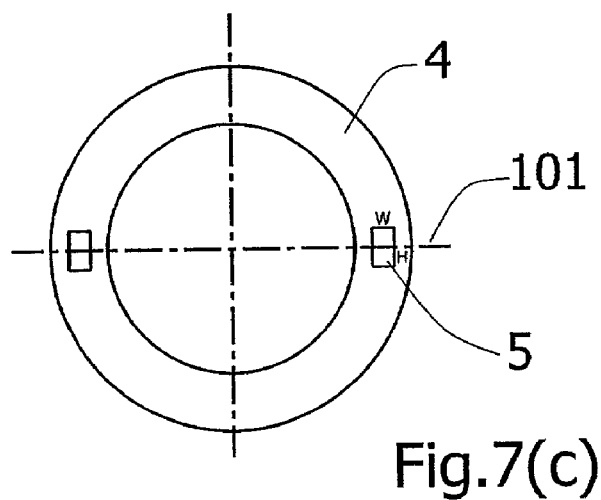

Referring to FIGS. 9(a) to 9(y) there is illustrated a catheter according to the invention being inserted through a section of a vasculature V. The section of vasculature is illustrated schematically and comprises a first simple 2D bend $B_1$, and a second more complex bend $B_2$ leading to a side branch S. The catheter 1 in this case is of the type illustrated in FIG. 7(c).

Referring to FIG. 9(a) the catheter shaft is first advanced by the user in the "Z" direction which need be the only direction of force applied by the user. At this stage the catheter shaft is in a state of disorientation with regard to the position of the reinforcement wires 5 relative to the vessel V. Thus the catheter shaft advances in whatever orientation it was inserted into the vessel.

Section A—A is a 2-dimensional plane view showing the cross section of both the vessel V and catheter shaft. This 2-D section is looking in the "Z" direction and illustrates the orientation of the reinforcement wires.

As the catheter shaft is advanced, it negotiates the first bend $B_1$ (on the Z-X Plane) as illustrated in FIG. 9(b). As the catheter approaches the 90 degree stage of the bend $B_1$, the reinforcement wires 5 begin to align themselves along the plane of neutral bending. Since there is no proximal resistance at the user end, this alignment of the reinforcement wires causes the entire catheter shaft to spontaneously torque itself.

2-D Section A1—A1 is a sectional plane pre 90° and illustrates the reinforcement wires 5 orienting towards the plane of neutral bend hence the spontaneous torqueing of the catheter shaft. 2-D Section A—A illustrates the spontaneous torqueing of the shaft along its entire length at this stage.

As the catheter shaft advances and reaches the apex of the bend $B_1$ the reinforcement wires 5 will have almost completed their alignment with the neutral plane of bending as illustrated in FIG. 9(b).

2-D Section A2—A2 looking in the "X" direction illustrates the reinforcement wires 5 orienting along the plane of neutral bending. 2-D Section A—A illustrates the reinforcement wires 5 orienting along the neutral plane of bending at the user end.

Referring to FIG. 9(d), as the catheter is advanced through the bend $B_1$ the reinforcement wires 5 align themselves along the plane of neutral bending resulting in the entire catheter shaft torqueing to allow this alignment making the distal section of the shaft more trackable. 2-D Section A3—A3 is a section plane post 90° and illustrates the orientation of the reinforcement wires 5 on the neutral plane of bending. 2-D Section A—A illustrates the orientation of the reinforcement wires 5 along the neutral plane of bending.

As the catheter shaft is advanced further to complete the bend (FIG. 9(e)) the reinforcement wires 5 remain oriented along the plane of neutral bending. 2-D Section A4—A4 looking in the "Z" direction illustrates the reinforcement wires 5 oriented along the plane of neutral bending. 2-D Section A—A which is also looking in the "Z" direction illustrates the reinforcement wires 5 oriented along the plane of neutral bending.

Referring to FIG. 9(f), as the user advances the catheter shaft further to the point at which it negotiates the second bend $B_2$ in the "Y" direction, the reinforcement wires 5 begin to align themselves with the plane of neutral bending for this bend. However the first bend now provides the catheter shaft with some proximal resistance preventing the entire shaft from torqueing. This proximal resistance coupled with the reinforcement wires 5 tending to align along the neutral plane of bending of the second bend, causes the catheter shaft to spontaneously twist. This spontaneous twisting of the catheter shaft is localised in the zone indicated. 2-D Section A5—A5 looking in the "Z" direction illustrates the reinforcement wires 5 orienting themselves with the neutral plane. 2-D Section A4—A4 illustrates the reinforcement wires 5 remaining aligned with the plane of neutral bending from the first bend.

As the user continues to advance the catheter shaft towards the apex of the second bend $B_2$ (FIG. 9(g)), the reinforcement wires 5 will have almost completed their alignment with the neutral plane of bending of the second bend $B_2$. 2-D Section A6—A6 illustrates an alignment of the reinforcement wires 5 with the neutral axis. In practice the reinforcement wires 5 tendency to align with the neutral plane of bending will result in them aligning very close to the neutral plane. 2-D Section A5—A5 looking in the "Z" direction illustrates the reinforcement wires 5 orienting themselves with the neutral plane of the second bend $B_2$. 2-D Section A4—A4 illustrates the reinforcement wires remaining aligned with the plane of neutral bending from the first bend $B_1$ as the catheter shaft advances further.

Referring to FIG. 9(h), as the catheter shaft is advanced further to complete the second bend the reinforcement wires 5 remain oriented along the plane of neutral bending of the second bend $B_2$. 2-D Section A7—A7 looking in the "Y" direction illustrates the reinforcement wires 5 oriented along the plane of neutral bending of the second bend $B_2$. 2-D Section A—A and 2-D Section A4—A4 illustrate the reinforcement wires 5 remaining aligned with the plane of neutral bending from the first bend when the catheter shaft has completed advancement.

It will be noted that torqueing and twisting of the catheter shaft occurs spontaneously, the user when advancing the catheter shaft need only apply a push force in the "Z" direction.

Figure 10A:
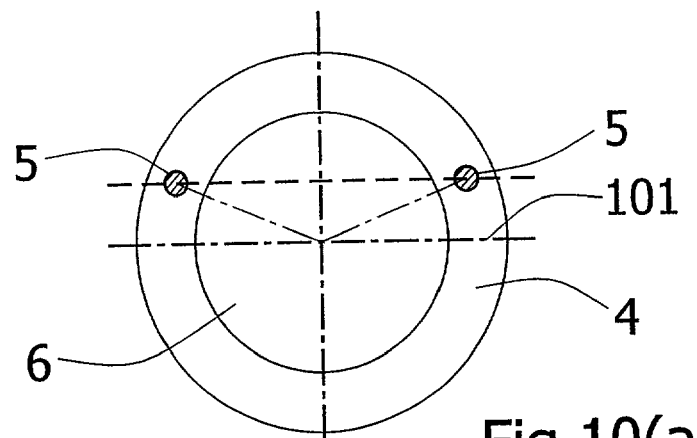
FIGS. 10(a) to 10(c) are end views of other catheters according to the invention.

It will be appreciated that it is not essential that the reinforcement wires 5 be positioned in the catheter body 4 on opposite sides of the catheter longitudinal axis opposed to one another by exactly 180 degrees. The reinforcements 5 may also be positioned on opposite sides of the catheter longitudinal axis opposed to one another by other angles, as illustrated in FIG. 10(a).

It has been found that by positioning the reinforcements 5 such that they are opposed to one another by an angle in the range between the points of inflection of the curve of FIG. 8 either side of 180 degrees, for example from 140 degrees to 220 degrees, more preferably from 160 degrees to 200 degrees, and ideally 180 degrees, a substantial reduction in the second moment of area of the reinforcements 5 and hence the second moment of area of the entire catheter around the neutral axis 101 will be achieved. In this manner, the force required to bend the catheter is substantially reduced, and thus greater trackability of the catheter is achieved to enable navigation through potentially narrow and/or tortuous passageways.

Figure 10B:
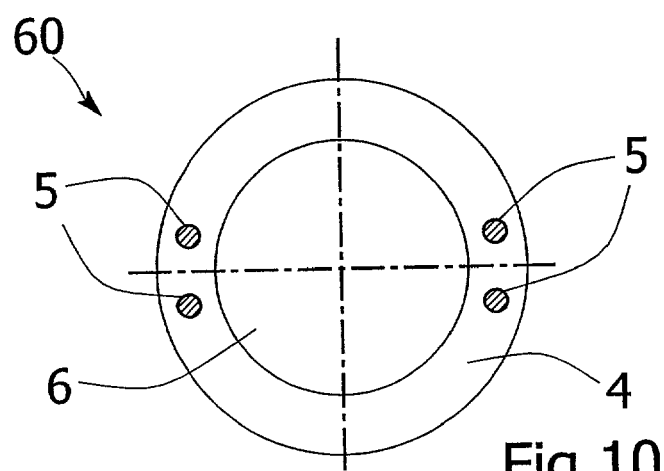

Referring now to FIG. 10(b), there is illustrated another catheter 60 according to the invention, which is similar to the catheter 1 of FIGS. 1 to 7, and similar elements in FIG. 10b) are assigned the same reference numerals.

In this case, each reinforcement comprises a cluster of two reinforcing elements, with each reinforcing element being provided by a reinforcement wire 5. Each pair of reinforcements 5 is grouped together on opposite sides of the catheter body 4 to form the cluster of two wires 5, the two clusters being diametrically opposed to each other, as illustrated in FIG. 10(b). Each cluster is narrow relative to the circumference of the catheter body 4.

As illustrated in FIG. 10(b), the two wires 5 in each cluster are located in the catheter body 4 at substantially the same radial distance from the longitudinal axis of the catheter 60.

The wire cluster arrangement enables a relatively large cross-sectional area of wire to be used which gives enhanced pushability, while maintaining adequate bonding between the catheter body 4 and the reinforcement wires 5. Thus the structural integrity of the catheter 60 is not adversely affected by a large cross-sectional area of wire.

Figure 10C:
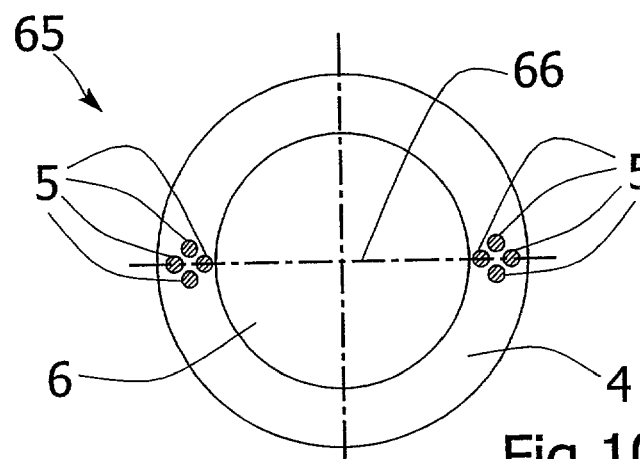

It will be appreciated that any suitable number of reinforcement wires 5 may be provided in each cluster, such as four wires 5 in each diametrically opposed cluster, as illustrated in the catheter 65 of FIG. 10(c). In this case, the wires 5 are clustered into a square with each wire 5 at a corner of the square. A diagonal 66 of the square cluster passes through the longitudinal axis of the catheter 65 (FIG. 10(c)).

The reinforcing elements in each cluster may be independent of one another and may be held in place by means of the surrounding over-extruded catheter body 4 only.

Alternatively, the reinforcing elements in each cluster may be interconnected by any suitable means, such as by braiding the reinforcement wires 5 together, as illustrated in FIGS. 11(a) and 11(b). Such a braided arrangement provides enhanced trackability for the catheter during advancement through a vasculature. The braided reinforcements 5 also have enhanced kink resistance.

It will be understood that the material of each or reinforcing element in each cluster may be of the same material or of different materials. In addition, the reinforcing elements in a cluster may be a mixture of different types of reinforcing elements, such as a mixture of wires, carbon fibres, sections of hard polymeric material.

Figure 12:
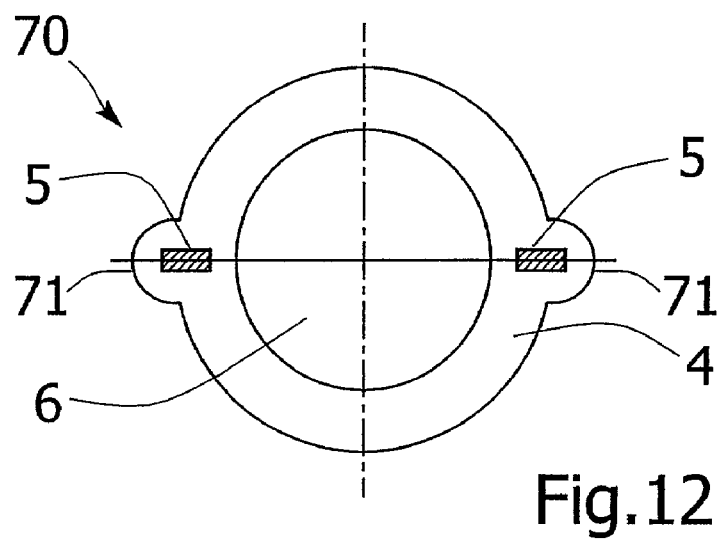

In FIG. 12, another catheter 70 according to the invention is illustrated, which is similar to the catheter 1 of FIGS. 1 to 8, and similar elements in FIG. 12 are assigned the same reference numerals.

In this case, the catheter body 4 is oversized around the reinforcements 5. The outer surface of the catheter body 4 is non-circular with two protruding ridges 71 on each side of the catheter body 4. The bulging ridges 71 enable larger reinforcements 5 to be used while ensuring the reinforcements 5 are completely embedded within the catheter body 4.

In addition, the ridges 71 act to reduce the frictional force acting between the catheter 70 and a vasculature wall during advancement of the catheter 70 through a vasculature by reducing the area of contact between the catheter 70 and the vasculature wall. Also the ridges 71 have a smooth outer surface and are shaped for a smooth crossing profile.

Figure 13:
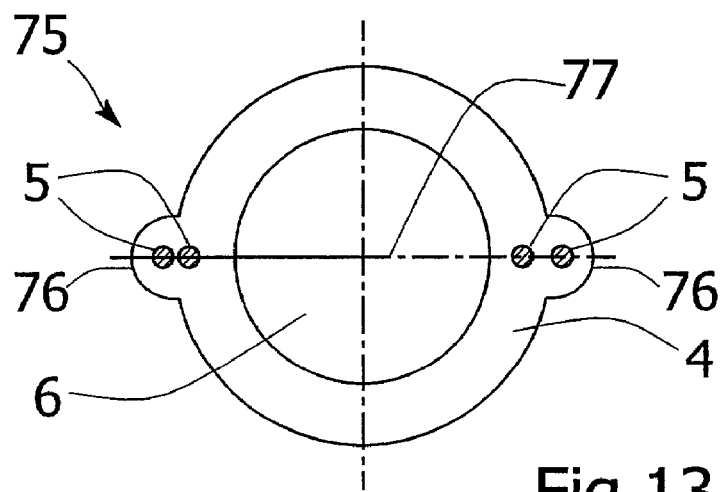

As illustrated in the catheter 75 of FIG. 13, the protruding ridges 76 are particularly advantageous in maintaining the reinforcements 5 completely embedded within the catheter body 4 when a cluster of reinforcement wires 5 is used. In this case, the two wires 5 are located in the catheter body 4 radially aligned along a radial line 77 which passes through the longitudinal axis of the catheter 75 and the two wires 5.

Figure 14:
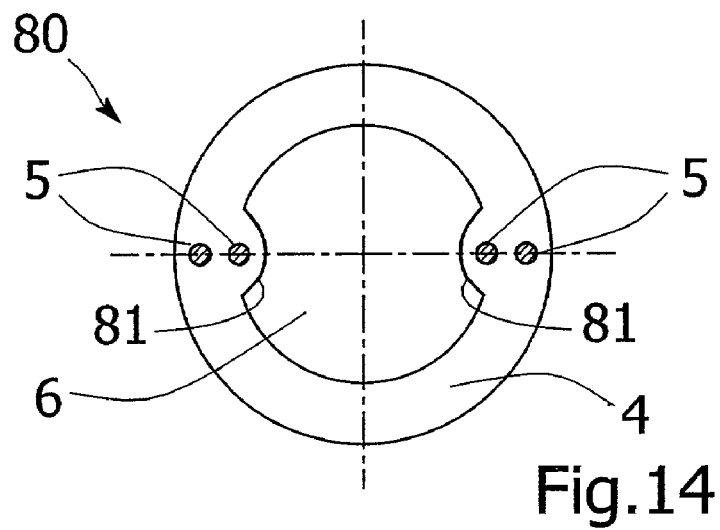

Inwardly protruding ridges 81 may be provided on the internal surface of the catheter body 4 in addition to or as an alternative to on the external surface, as illustrated in the catheter 80 of FIG. 14.

The internal ridges 81 act to reduce the frictional force acting between the catheter 80 and a guidewire, or the like, passing through the inner lumen 6 by reducing the area of contact between the catheter 80 and the guidewire.

FIG. 15(*b*) illustrates another catheter 90 according to the invention, which is similar to the catheter 1 of FIGS. 1 to 8, and similar elements in FIG. 15(*b*) are assigned the same reference numerals. In the case of catheter 90, the reinforcements 5 are substantially triangular in cross-section, as illustrated in FIG. 15(*b*).

In the case of the catheter 315 of FIG. 15(*a*), the reinforcements 5 are generally round in cross-section. These round reinforcements 5 have the advantage that the orientation that the reinforcements 5 take up in the catheter body 4 do not have to be controlled. However the round reinforcements do not provide the same second moment of area benefits as the rectangular reinforcements of FIGS. 1 to 8.

It will be appreciated that numerous other cross-sectional shapes are possible for the reinforcements 5. The performance characteristics of the catheter may be controlled to an extent by a suitable choice of the shape of the reinforcement 5.

A sample range of possible shapes is illustrated in FIG. 16. The "I" shaped cross-section illustrated in FIG. 16(*e*) is a particularly preferred option. In use, the "I" shaped reinforcement 5 is aligned with the end parts of the "I" substantially parallel with a radial line 91 which passes through the longitudinal axis of the catheter and the reinforcement 5.

Some of these alternative shapes have an increased area of contact with the catheter body 4 and thus have improved adhesion between the catheter body 4 and the reinforcement 5. Manufacturing difficulties may however arise with some of the more intricate profiles.

For example, in the catheter 95 of FIG. 17 the rectangular reinforcement 5 is aligned with the long side of the rectangle substantially parallel to a radial line 96 which passes through the longitudinal axis of the catheter 95 and the reinforcement 5. Thus the reinforcements 5 in the catheter 95 of FIG. 17 have a relatively large length L and a relatively small width W (FIG. 18). This contrasts with the catheter 1 of FIG. 19, in which the reinforcement 5 is aligned with the short side of the rectangle substantially parallel to the radial line 96. Thus the reinforcements 5 in the catheter 1 of FIG. 19 have a relatively small length L and relatively large width W. The reinforcements of FIG. 18 therefore provide the same pushability for the catheter 95, but the second moment of area of the catheter 95 of FIG. 18 about the neutral axis 101 is reduced relative to the second moment of area of catheter 1 of FIG. 19 about the neutral axis 101. In this manner, the narrow reinforcements of FIG. 18 further reduce the resistance to trackability of the catheter 95 compared to the catheter 1 of FIG. 19.

In general both round and rectangular wires are usually stock profiles and thus will be readily available as drawn wires. This is one reason why wires of these sections are preferred.

Figure 20:
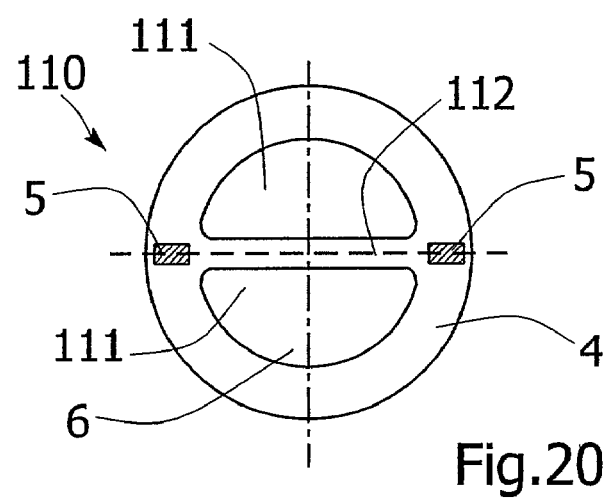
FIG. 20 is an end view of a further catheter according to the invention.
Figure 21:
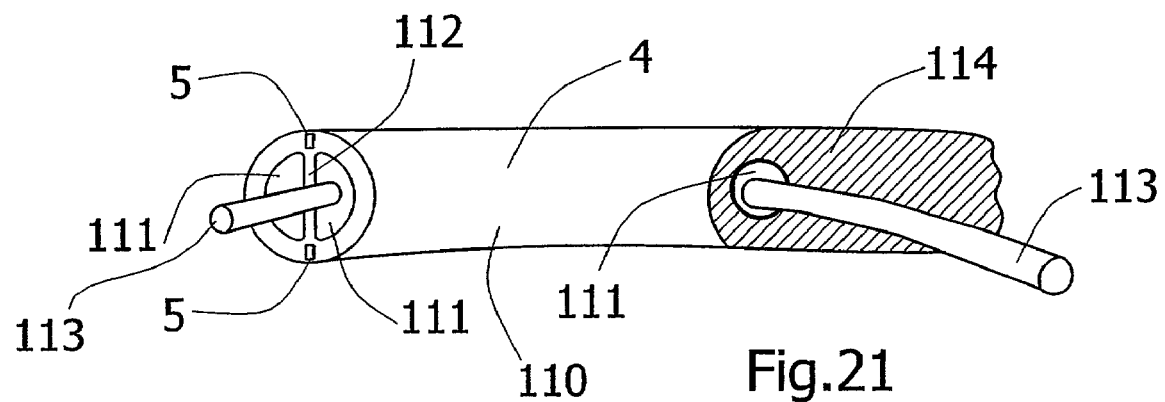
FIG. 21 is a perspective view of the catheter of FIG. 20 in use.

Referring to FIGS. 20 and 21, there is illustrated another catheter 110 according to the invention, which is similar to the catheter 1 of FIGS. 1 to 8, and similar elements in FIGS. 20 and 21 are assigned the same reference numerals.

In this case, the catheter 110 comprises two inner lumena 111 separated by an arm 112. As illustrated in FIG. 20, the separator arm 112 is aligned along the same plane as the diametrically opposed reinforcements 5. Therefore the separator arm 112 will be aligned along the plane of neutral bending during advancement. Thus the adverse effect of the separator arm 112 on the trackability of the catheter 110 is minimised.

This catheter 110 is particularly suitable for use in rapid exchange. Referring to FIG. 21 the catheter 110 is shown in use with a guidewire 113 in position extending through one of the inner lumen 111. The guidewire 113 exits the guidewire lumen 111 at a proximal end through a skive surface 114. This catheter construction allows the reinforcements 5 and the separator arm 112 to be largely unaffected by the skiving operation. Indeed, the presence of the reinforcements 5 makes identifying the skive surface 114 easier as the catheter 110 automatically aligns the reinforcement plane when bent.

In FIGS. 22 to 38 there are illustrated various embodiments of catheter according to the invention in which the reinforcements 5 are connected by a connection piece 116. Such a connection piece 116 has the advantage of ease of manufacture in that the reinforcements 5 may be located relative to one another during manufacturing in a desired position with a desired angular orientation.

FIG. 22 illustrates another catheter 115 according to the invention, which is similar to the catheter 1 of FIGS. 1 to 8, and similar elements in FIG. 22 are assigned the same reference numerals.

The catheter 115 comprises a connection piece 116 which extends circumferentially around the catheter body 4 to interconnect the two reinforcement wires 5 in both directions. The connection piece 116 also extends longitudinally along the catheter 115.

The reinforcement wires 5 are integrally formed with the connection piece 116. In this manner, the position of the two wires 5 relative to one another may be accurately and easily controlled, so that the reinforcements 5 will oppose one another at a predetermined specific angle, such as 180 degrees. In addition, the shape of the reinforcements 5 may be accurately defined.

The catheter 115 with the connection piece 116 is longitudinally twistable as described previously to enable the reinforcements 5 to align themselves along the neutral axis 101 as the catheter 115 is advanced through a body passageway.

The connection piece 116 is provided on the internal surface of the catheter body 4, and thus forms a low-friction tubular sheath to minimise friction between a guidewire in the inner lumen 6 and the catheter 115.

By locating the connection piece 116 along the internal surface of the catheter body 4, the second moment of area of the connection piece 116 around the neutral axis 101 is minimised. Thus the force required to bend the connection piece 116 during advancement through a body passageway is also minimised. By locating the connection piece 116 along the internal surface of the catheter body 4, it is also easier to torque the catheter 115 in a tortuous passageway.

It will be appreciated that the connection piece 116 may be used to interconnect the reinforcements 5 for any suitable shape of reinforcement 5, as illustrated in the catheter 120 of FIG. 23.

In the catheter 125 of FIG. 24, the reinforcements 5 protrude inwardly into the inner lumen 6. This configuration acts to minimise the frictional force acting between the catheter 125 and a guidewire passing through the inner lumen 6 by minimising the area of contact between the catheter 125 and the guidewire.

Similarly the reinforcements 5 protrude outwardly from the external surface of the catheter 125 to minimise the frictional force acting between the catheter 125 and a vasculature wall during advancement of the catheter 125 through the vasculature. In addition, the protruding reinforcements 5 have a smooth surface and are shaped for a smooth crossing profile.

The connection piece 116 may extend only partially circumferentially around the catheter body 4 to interconnect the two reinforcements 5 in one direction only, as illustrated in the catheter 130 of FIG. 25.

It will be appreciated that any suitable configuration of reinforcement 5 may be used with the semi-circular connection piece 116, such as reinforcements 5 that protrude inwardly and outwardly, as illustrated in the catheter 135 of FIG. 26.

Referring to FIG. 27, there is illustrated another catheter 140 according to the invention, which is similar to the catheter 115 of FIG. 22, and similar elements in FIG. 27 are assigned the same reference numerals.

In this case, the tubular connection piece 116 is completely embedded within the catheter body 4, and the connection piece 116 does not protrude into the inner lumen 6. This configuration permits the material of the catheter body 4 on the inner and outer surfaces of the catheter 140 to be tailored as desired. Also by embedding the connection piece 116 within the catheter body 4, a more secure adhesion of the connection piece 116 with the catheter body 4 will be achieved.

The reinforcements 5 may be of any suitable shape, as illustrated in the catheter 145 of FIG. 28.

Furthermore, the reinforcements 5 may protrude outwardly from the external surface of the catheter 150, as illustrated in FIG. 29. In this manner, the frictional force acting between the catheter 150 and a vasculature wall during advancement of the catheter 150 through the vasculature is minimised.

The reinforcements 5 may Alternatively protrude inwardly into the inner lumen 6, as illustrated in FIG. 31. This configuration acts to minimise the frictional force acting between the catheter 160 and a guidewire passing through the inner lumen 6.

As a further alternative, the reinforcements 5 may protrude both outwardly from the external surface of the catheter 155 and inwardly into the inner lumen 6, as illustrated in FIG. 30.

It will be appreciated that the connection piece 116 may extend only partially circumferentially around the catheter body 4 to interconnect the two reinforcements 5 in one direction only, as illustrated in the catheter 165 of FIG. 32.

In the catheter 170 illustrated in FIG. 33, the reinforcements 5 are positioned such that they are on opposite sides of the longitudinal axis of the catheter 170 opposed to one another by an angle other than 180 degrees, in this case approximately 140 degrees. The interconnection piece 116 extends between the two reinforcements 5 to interconnect the reinforcements 5 in one direction.

FIG. 34 illustrates another catheter 175 according to the invention, which is similar to the catheter 115 of FIG. 22, and similar elements in FIG. 34 are assigned the same reference numerals.

The connection piece 116 is provided on the external surface of the catheter body 4 to form a low-friction tubular sheath to minimise friction between the catheter 175 and a vasculature wall during advancement of the catheter 175 through the vasculature.

The reinforcements 5 may protrude inwardly, or outwardly, or both inwardly and outwardly (FIG. 35) to minimise frictional forces acting on the catheter 180.

It will further be appreciated that the connection piece 116 may extend only partially circumferentially around the catheter body 4 to interconnect the two reinforcements 5 in one direction only, as illustrated in the catheter 185 of FIG. 36.

In FIG. 37, there is illustrated another catheter 190 according to the invention, which is similar to the catheter 115 of FIG. 22, and similar elements in FIG. 37 are assigned the same reference numerals.

In this case, the connection piece 116 extends as a chord directly across the inner lumen 6 to interconnect the two reinforcements 5. By extending across the inner lumen 6, the connection piece 116 divides the inner lumen 6 into two lumena similar to the catheter 110 of FIGS. 20 and 21.

In use, the reinforcements 5 align themselves along the plane of neutral bending. The connection piece 116 is aligned along a line 191 which passes through the two reinforcements 5. Therefore the connection piece 116 will also be aligned along the plane of neutral bending during advancement. Thus the adverse effect of the connection piece 116 on the trackability of the catheter 190 is minimised.

It will be appreciated that any suitably shaped reinforcement 5 may be used with the chord-like connection piece 116, as illustrated in the catheter 195 of FIG. 38, in which the reinforcements 5 have a generally annular cross-section.

It will be appreciated that for any of the catheters described previously with reference to FIGS. 22 to 38, the connection piece 116 may be provided at a number of discrete locations along the catheter only, in a configuration similar to a ladder.

The reinforcements 5 may be fixed to the catheter body 4 by any suitable means. Over-extrusion is a highly cost effective and practical means of fixing, however it is not essential to over-extrude the catheter body 4 onto the reinforcements 5. For example the reinforcements 5 could be bonded or welded to the internal surface of the catheter body 4 after the catheter body 4 has been extruded, as illustrated in the catheter 200 of FIG. 39. Alternatively the reinforcements 5 could be bonded or welded to the external surface of the catheter body 4 after the catheter body 4 has been extruded, as illustrated in the catheter 205 of FIG. 40.

Further possible fixing means include dip casting, overmoulding, solution casting, multi-lumen extruding and bonding, and heat shrinking to fix the reinforcements 5 to the catheter body 4. In solution casting, the catheter body 4 is solution cast over a mandrel with the reinforcements 5 in place. However this is an expensive method and is limited to certain materials. During multi-lumen extruding and bonding, the reinforcements 5 are passed through the catheter body 4 and bonded into place.

Achieving the necessary adhesion along the length of the catheter may however be difficult. In heat shrinking, a sleeve is located around the catheter body 4 with the reinforcements 5 in place. The sleeve is then heat shrunk to fasten the reinforcements 5 in place. Adhesion between the catheter body 4 and the reinforcements 5 may prove difficult to achieve along the length of the catheter using this method.

It is not essential that stainless steel be used for the reinforcement 5, the reinforcements 5 may be of any suitable material such as nitinol, or kevlar, or carbon fibre. Nitinol is highly recoverable when positioned in a very tortuous body passageway, but is a more expensive material than stainless steel and has a lower elastic compressive modulus than stainless steel. Kevlar and carbon fibre are particularly useful in non-magnetic applications, but also are expensive materials due to non-standard processing.

It will be appreciated that it is not essential that a metallic wire be used for the reinforcement 5.

FIG. 41 illustrates another catheter 210 according to the invention, which is similar to the catheter 1 of FIGS. 1 to 8, and similar elements in FIG. 41 are assigned the same reference numerals.

In this case, the reinforcements 211 comprise a section of a suitably hard polymeric material. Because both the reinforcements 211 and the catheter body 4 are of polymeric materials, the catheter body 4 and the reinforcements 211 can be co-extruded together to form the catheter 210. Co-extrusion is a particularly suitable forming process to use when the reinforcements 211 are of a polymeric material.

In addition, co-extrusion enables the catheter to be formed with a layered structure of different materials. This enables the catheter to have selected surface properties, such as low friction, on inside or outside layers.

It will be appreciated that the catheter body 4 and the reinforcements 211 may be of different polymeric materials, or of the same polymeric material.

The polymeric reinforcements 211 are open to the external surface of the catheter 210 and to the internal surface of the catheter 210.

Alternatively the polymeric reinforcements 221 may be completely embedded within the catheter body 4, as illustrated in the catheter 220 of FIG. 43.

The polymeric reinforcements 216 may be provided on the external surface of the catheter 215 protruding outwardly, as illustrated in FIG. 42, to minimise the frictional force acting between the catheter 215 and a vasculature wall during advancement of the catheter 215 through the vasculature.

The polymeric reinforcements 226 may Alternatively be provided on the internal surface of the catheter 225 protruding inwardly into the inner lumen 6, as illustrated in FIG. 44, to minimise the frictional force acting between the catheter 225 and a guidewire passing through the inner lumen 6.

Polymeric reinforcements are particularly useful in non-magnetic applications, however a larger cross-sectional area of polymeric reinforcement is needed to achieve the necessary push than with the stainless steel reinforcements as discussed previously.

Figure 45:
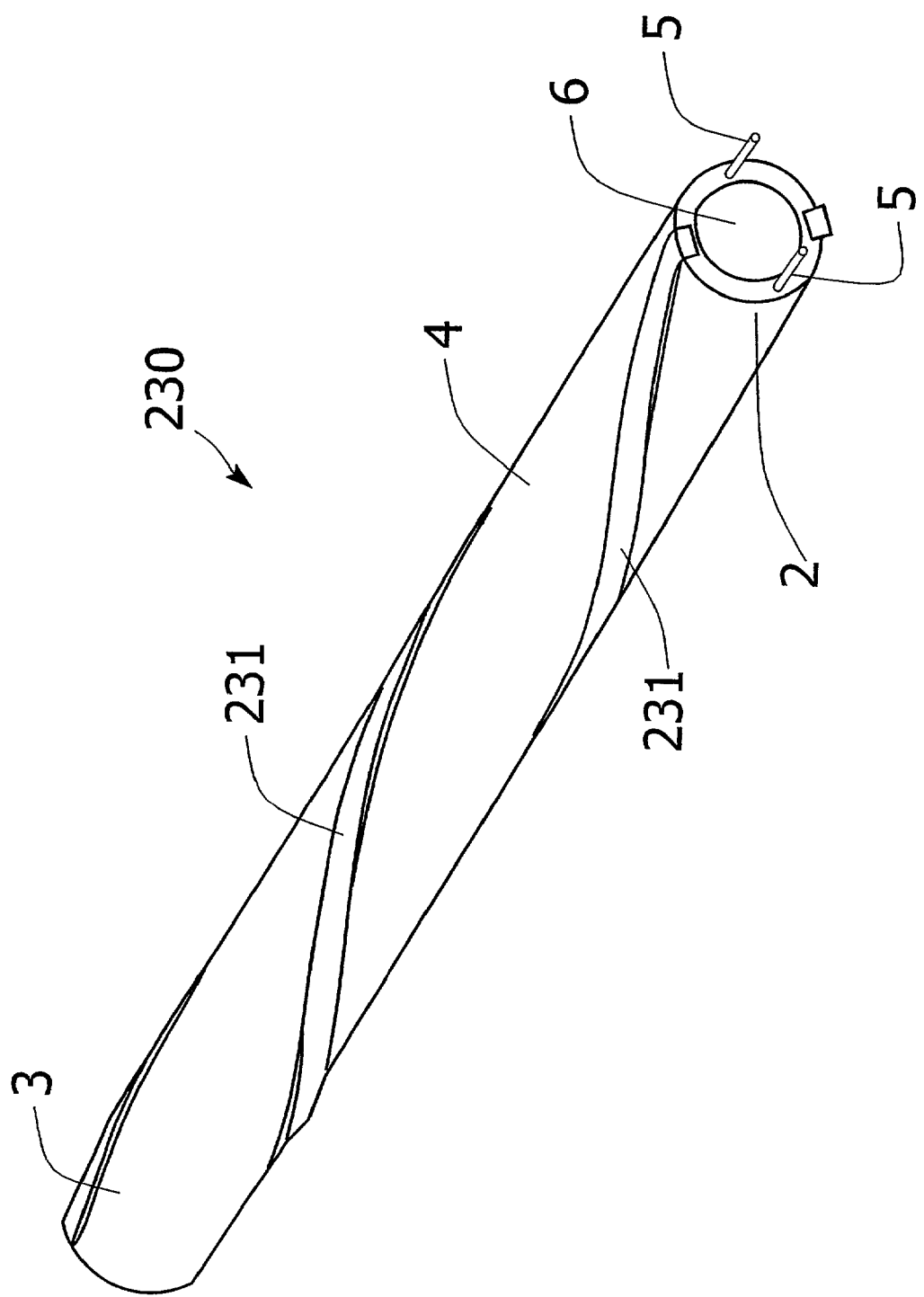
FIG. 45 is a perspective view of another catheter according to the invention.

FIG. 45 illustrates a further catheter 230 according to the invention, which is similar to the catheter 1 of FIGS. 1 to 8, and similar elements in FIG. 45 are assigned the same reference numerals. The catheter 230 comprises two reinforcement columns 231 extending along the catheter body 4 in a spiral (FIG. 45). The spiral columns 231 enhance the radial strength of the catheter 230, and provide kink resistance during advancement of the catheter 230 through a vasculature.

The columns 231 are partially embedded in the catheter body 4 and are open to the external surface of the catheter 230.

Figure 46:
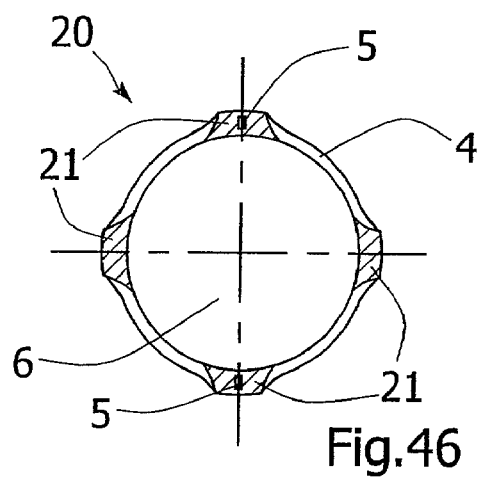
FIGS. 46 to 49 are end views of further catheters according to the invention.
Figure 47:
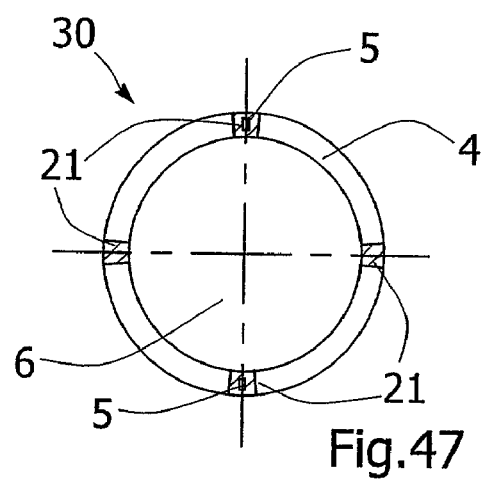

Referring to FIGS. 46 and 47 there are illustrated further catheters 20, 30 respectively according to the invention, which are similar to the catheter 1 of FIGS. 1 to 8, and like reference numerals are assigned to similar elements in FIGS. 46 and 47. The catheters 20, 30 comprise at least one, and in these cases four reinforcement columns 21 extending longitudinally along the catheter body 4 to minimise the possibility of buckling of the catheters 20, 30 during advancement through a body passageway.

The cross sections of the columns 21 are shaped to define high second moments of area, and the columns 21 are of a material which is stiff relative to the flexible catheter body 4. This ensures a high critical buckling load for the reinforcement columns 21 to minimise the possibility of buckling of the catheters 20, 30 during advancement.

The columns 21 are equi-spaced apart circumferentially around the catheter body 4 to minimise the possibility of circumferential buckling of the catheters 20, 30.

The catheters 20, 30 of FIGS. 46 and 47 respectively have reinforcement columns 21 of different cross-sectional shapes. It will be appreciated that a variety of different shapes are possible for the reinforcement columns 21. For example, in another embodiment of the invention the cross section of the reinforcement columns 21 may be substantially I-shaped for a particularly high second moment of area.

In FIG. 10, the reinforcement columns 21 are partially embedded in the catheter body 4, and protrude radially outwardly of the catheter body 4 to define four low-friction guides which facilitate ease of relative movement of the catheter 20 through a body passageway.

It will be appreciated that the columns 21 may Alternatively or additionally extend radially inwardly of the catheter body 4 to define low-friction guides for ease of passage of an article, such as a guidewire or a retrieved embolic protection filter, through the inner lumen 6.

Figure 48:
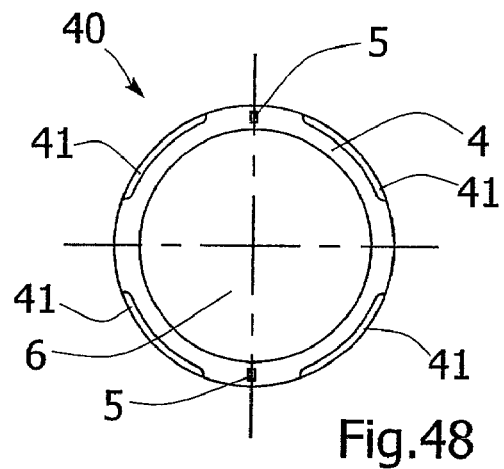
Figure 49:
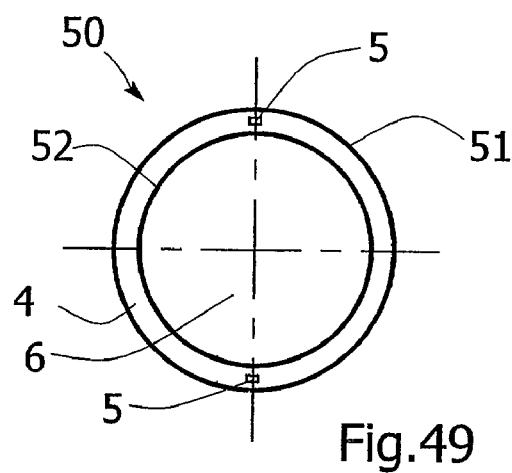

Referring to FIGS. 48 and 49 there are illustrated further catheters 40, 50 respectively according to the invention, which are similar to the catheter 1 of FIGS. 1 to 8, and like reference numerals are assigned to similar elements in FIGS. 48 and 49. In these cases the catheters 40, 50 comprise one or more guides to ease passage of the catheters 40, 50 through a body passageway and/or to ease passage of an article, such as a guidewire or a retrieved embolic protection filter, through the inner lumen 6.

With particular reference initially to FIG. 48, the one or more guides in this case are provided by four arcuate protrusions 41 extending radially outwardly on the external surface of the catheter body 4, and extending longitudinally along the catheter body 4. The protrusions 41 extend partially circumferentially around the catheter body 4 (FIG. 48), and the protrusions 41 are of a low coefficient of friction material. Suitable low friction materials include Pellethane or a nylon material, or a fluoropolymer material, or a polyethylene material, or a polypropylene polyolefin material.

In use, the low friction protrusions 41 engage the walls of the passageway through which the catheter 40 passes, and in this manner the protrusions 41 facilitate ease of passage of the catheter 40 through the passageway.

Referring now to FIG. 49, the one or more guides comprise an outwardly extending protrusion 51 and an inwardly extending protrusion 52. Both protrusions 51, 52 extend longitudinally at least partially along the length of the catheter body 4, and extend circumferentially completely around the external surface of the catheter body 4 to define an outer tubular sheath and circumferentially completely around the internal surface of the catheter body 4 to define an inner tubular sheath (FIG. 49). Both of the protrusions 51, 52 are of a suitable, low coefficient of friction material.

In use, the low friction outer sheath engages the walls of the passageway through which the catheter 50 passes, and in this way facilitates ease of passage of the catheter 50 through the passageway. The low friction inner sheath engages with an article passing through the inner lumen 6, and in this way facilitates ease of passage of the article through the inner lumen 6.

The catheter of the invention may comprise means to facilitate rapid exchange of the catheter over a guidewire, the means typically being provided by an opening in the catheter body 4 which defines a rapid exchange port in communication with a guidewire lumen, the guidewire lumen extending only partially through the catheter from the distal end of the catheter to the rapid exchange port.

The reinforcements 5 may extend along the entire length 301 of the catheter 300, as illustrated in FIG. 50, from the proximal end 2 to the distal end 3. Alternatively the reinforcements 5 may extend along only part 306 of the length of the catheter 305, as illustrated in FIG. 51. For example in the case of a rapid exchange catheter 307, as illustrated in FIG. 52, it may only be necessary to provide the reinforcements 5 extending along a part 308 of the catheter 307 distally of the rapid exchange port 309 to the distal end 3 of the catheter 307. The catheters 300, 305 of FIGS. 50 and 51 are over-the-wire systems.

Figure 53:
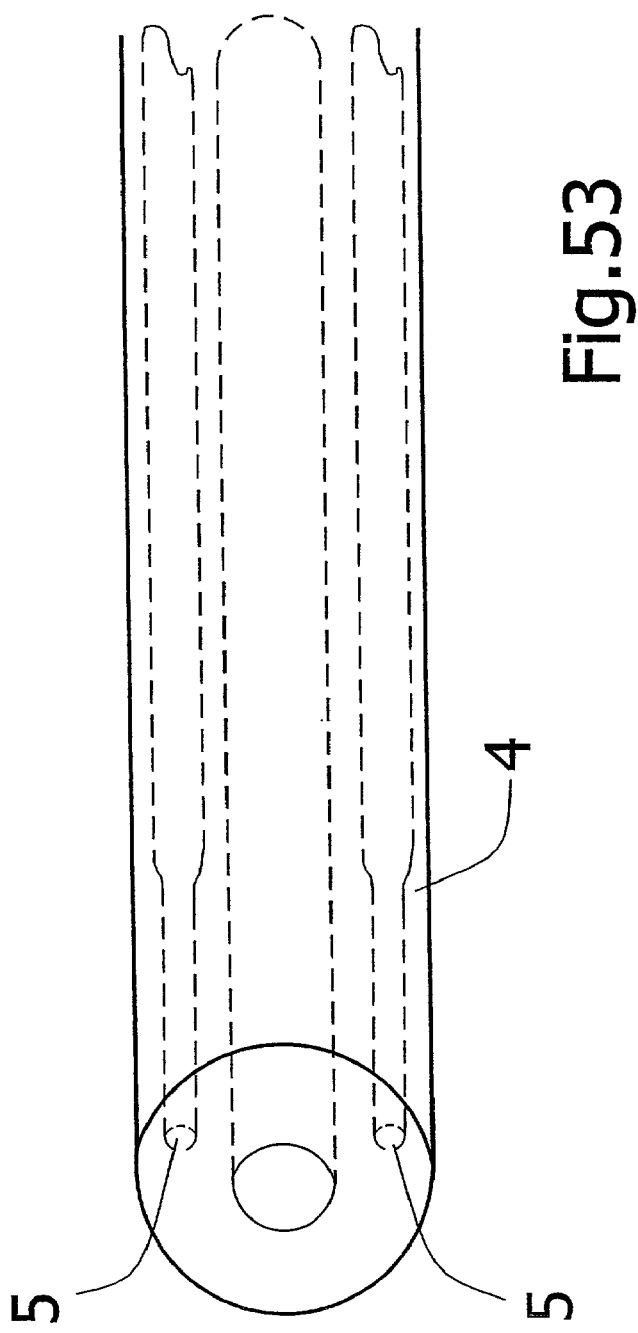
FIGS. 53 and 54 are perspective views of further catheters according to the invention.
Figure 54:
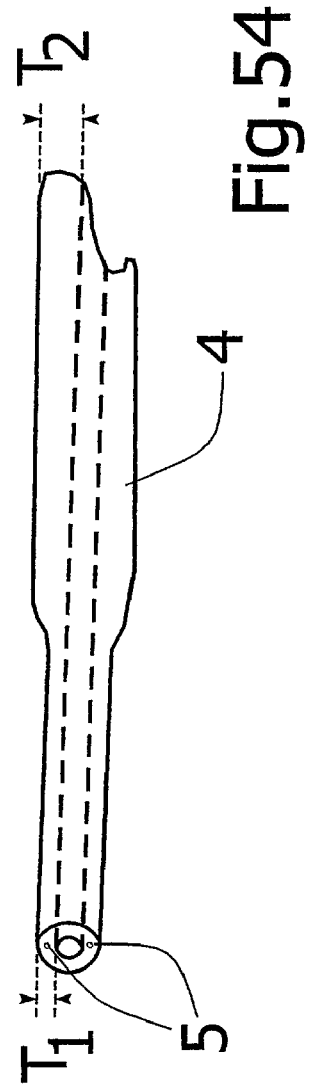

It will be understood that the cross-sectional area of the catheter body 4 and/or the cross-sectional area of the reinforcements 5 do not need to be uniform along the length of the catheter. As illustrated in FIG. 53, the cross-sectional area of the reinforcements 5 may vary along the length of the catheter. Alternatively the cross-sectional area of the catheter body 4 may vary along the length of the catheter from a smaller wall thickness $T_1$ to a larger wall thickness $T_2$. By varying the cross-sectional areas, the mechanical properties of the catheter, such as pushability and trackability, at particular locations along the length of the catheter may be accurately controlled.

The catheter of the invention may comprise an expansible tip, usually of a flexible material, at the distal end of the catheter, for example for retrieving an article, such as an embolic protection filter, from a body passageway of a patient. The tip may be attached to the distal end of the catheter, for example by bonding the tip to the distal end.

The material for the tip and the material for the catheter body are selected to ensure a secure bond between the tip and the catheter body. The materials for the tip and the catheter body may be selected from the peba group of materials. Alternatively the materials may be selected from the polyurethane group of materials. As another alternative the materials may be selected from the fluoropolymer group of materials. As a further alternative the materials may be selected from the polyester group of materials.

It will be appreciated that the tip may be over-extruded with the catheter body over the reinforcements. Alternatively or additionally, the reinforcements may extend at least partially into the tip.

Alternatively the distal end of the catheter of the invention may itself act as an expansible tip for retrieving an article into the inner lumen.

The catheter may comprise means for centring of the catheter on a guidewire during advancement of the catheter through a body passageway, the means typically being provided by a centring catheter which protrudes distally of the distal end of the catheter during advancement. The centring catheter provides a smooth transition from a guidewire to the catheter minimising vessel trauma and/or preventing dislodgement of other medical devices, such as a stent, during advancement of the catheter through a body passageway. The centring catheter is retractable relative to the catheter after advancement, for example to facilitate retrieval of an article, such as an embolic protection filter, into the catheter.

An arrow-head shaped tip, or rounded tip, or ball-nose shaped tip may be provided on the centring catheter for a smooth crossing profile.

A hydrophilic coating is usually provided around the interior and/or exterior of the catheter. This results in at least reduction and in some cases substantial elimination of platelet adhesion and fibrin build-up which could otherwise at least partially occlude the catheter inner lumen and/or create a harmful thrombus. A hydrophilic coating also reduces the co-efficient of friction of the catheter for ease of advancement and/or retrieval.

The catheter may be used in a wide variety of applications. Because of the combined properties of trackability with pushability it can be used in a wide range of body passageways including, but not limited to, the vasculature. It could be used in the colon, for example. The catheter, by virtue of the spontaneous twisting effect described above can be pushed through simple two dimensional tortuosities such as C-shaped bends of more complex three dimensional tortuosities. This is particularly important in delivery and/or retrieval of the catheter to or from a location which, either because of the nature of the passageway or the anatomy of the patient generally, required passage through one or several tortuosities.

The catheter finds particular application in delivery and/or retrieval of medical devices such as stents, or especially embolic protection filters of the type described, for example in our co-pending applications WO-A-99 23976 and WO-A-01 80777. The catheter may be used as a delivery or retrieval catheter or as a centring catheter.

The catheter according to the invention may be used in a variety of different intravascular applications, for example as a retrieval catheter for retrieving an article, such as an embolic protection filter, or a kidney stone, from a location in a body passageway. In this case, the retrieval catheter is usually advanced over a pre-positioned guidewire in a body passageway so that no torqueing of the catheter by the user is required.

Alternatively the catheter according to the invention may be a delivery catheter for delivering a medical device to a desired location in a body. When high tensile forces are employed the catheter may be employed for deployment of medical devices such as an embolic protection filter, or a stent, or the like.

The catheter, because it is highly trackable, may be used as an angioplasty catheter. In this case the catheter may be used for an angioplasty balloon and/or for stent delivery, especially for a balloon expandable stent.

The catheter of the invention is also useful as a steering catheter, for example in electrophysiology.

Other means of varying the mechanical properties of the catheter are also possible, such as varying the materials of the reinforcements/catheter body along the length of the catheter.

The invention is not limited to the embodiments hereinbefore described, with reference to the accompanying drawings, which may be varied in construction and detail.

The invention claimed is:

1. A catheter for advancement through a body passageway, the catheter comprising:
   a flexible catheter body; and
   two reinforcements extending at least partially along the catheter body;

the two reinforcements being located on opposite sides of the longitudinal axis of the catheter, and the product $(EI_{max})_R$ of the Young's modulus and the maximum second moment of area of the reinforcement is greater than the product $(EI)_m$ of the Young's modulus and the second moment of area of the catheter body material.

2. A catheter as claimed in claim 1 wherein $(EI_{max})_R$ is at least 2 times greater than $(EI)_m$.

3. A catheter as claimed in claim 1 wherein $(EI_{max})_R$ is at least 4 times greater than $(EI)_m$.

4. A catheter as claimed in claim 1 wherein $(EI_{max})_R$ is at least 6 times greater than $(EI)_m$.

5. A catheter as claimed in claim 1 wherein $(EI_{max})_R$ is at least 8 times greater than $(EI)_m$.

6. A catheter as claimed in claim 1 wherein $(EI_{max})_R$ is at least 10 times greater than $(EI)_m$.

7. A catheter as claimed in claim 1 wherein the product $(EI)_m$ of the Young's modulus and the second moment of area of the catheter body material is greater than the product $(EI_{min})_R$ of the Young's modulus and the minimum second moment of area of the reinforcement.

8. A catheter as claimed in claim 7 wherein $(EI)_m$ is at least 10 times greater than $(EI_{min})_R$.

9. A catheter as claimed in claim 7 wherein $(EI)_m$ is at least 50 times greater than $(EI_{min})_R$.

10. A catheter as claimed in claim 7 wherein $(EI)_m$ is at least 100 times greater than $(EI_{min})_R$.

11. A catheter as claimed in claim 7 wherein $(EI)_m$ is at least 200 times greater than $(EI_{min})_R$.

12. A catheter as claimed in claim 1 wherein the Young's modulus of the reinforcement $E_R$ is substantially greater than the Young's modulus of the catheter body material $E_m$.

13. A catheter as claimed in claim 12 wherein $E_R$ is at least 20 times greater than $E_m$.

14. A catheter as claimed in claim 12 wherein $E_R$ is at least 100 times greater than $E_m$.

15. A catheter as claimed in claim 12 wherein $E_R$ is at least 1,000 times greater than $E_m$.

16. A catheter as claimed in claim 1 wherein a first radial line which passes through the longitudinal axis of the catheter and one reinforcement subtends an angle in the range of from 140 degrees to 180 degrees with a second radial line which passes through the longitudinal axis of the catheter and the other reinforcement.

17. A catheter as claimed in claim 16 wherein the first radial line subtends an angle in the range of from 160 degrees with the second radial line.

18. A catheter as claimed in claim 16 wherein the first radial line subtends an angle of approximately 180 degrees with the second radial line.

19. A catheter as claimed in claim 1 wherein the reinforcement is fixed relative to the catheter body.

20. A catheter as claimed in claim 19 wherein the reinforcement is at least partially embedded in the catheter body.

21. A catheter as claimed in claim 20 wherein the catheter body is oversized around the reinforcement.

22. A catheter as claimed in claim 1 wherein the reinforcement is provided at least partially on an external surface of the catheter body.

23. A catheter as claimed in claim 1 wherein the reinforcement is provided at least partially on an internal surface of the catheter body.

24. A catheter as claimed in claim 1 wherein the catheter body is over-extruded over the reinforcements.

25. A catheter as claimed in claim 1 wherein the reinforcement is of stainless steel, or nitinol, or kevlar, or carbon fibre.

26. A catheter as claimed in claim 1 wherein the reinforcement comprises a wire.

27. A catheter as claimed in claim 1 wherein the reinforcement comprises a spring.

28. A catheter as claimed in claim 1 wherein the reinforcement comprises a section of hard polymeric material.

29. A catheter as claimed in claim 1 wherein the reinforcement comprises a cluster of one or more reinforcing elements.

30. A catheter as claimed in claim 29 wherein the reinforcing elements are interconnected.

31. A catheter as claimed in claim 29 wherein the reinforcing elements are braided together.

32. A catheter as claimed in claim 29 wherein the reinforcing element comprises a wire.

33. A catheter as claimed in claim 32 wherein the reinforcement comprises a cluster of two wires.

34. A catheter as claimed in claim 33 wherein the two wires are located at substantially the same radial distance from the longitudinal axis of the catheter.

35. A catheter as claimed in claim 33 wherein the two wires are radially aligned along a radial line which passes through the longitudinal axis of the catheter and both wires.

36. A catheter as claimed in claim 32 wherein the reinforcement comprises a cluster of four wires.

37. A catheter as claimed in claim 36 wherein the four wires are clustered into a square with each wire at a corner of the square.

38. A catheter as claimed in claim 37 wherein a diagonal of the square passes through the longitudinal axis of the catheter.

39. A catheter as claimed in claim 32 wherein the wire is of stainless steel, or nitinol, or kevlar, or carbon fibre.

40. A catheter as claimed in claim 29 wherein the reinforcing element comprises a spring.

41. A catheter as claimed in claim 29 wherein the reinforcing element comprises a section of hard polymeric material.

42. A catheter as claimed in claim 1 wherein one reinforcement is interconnected with the other reinforcement by a connecting arm.

43. A catheter as claimed in claim 42 wherein the connecting arm extends at least partially circumferentially around the catheter body.

44. A catheter as claimed in claim 42 wherein the connecting arm extends at least partially as a chord across the catheter body.

45. A catheter as claimed in claim 44 wherein the connecting arm is aligned along a line which passes through the two reinforcements.

46. A catheter as claimed in claim 42 wherein the connecting arm extends longitudinally along the catheter.

47. A catheter as claimed in claim 42 wherein the connecting arm is provided at least partially on an external surface of the catheter body.

48. A catheter as claimed in claim 42 wherein the connecting arm is provided at least partially on an internal surface of the catheter body.

49. A catheter as claimed in claim 42 wherein the connecting arm is at least partially embedded in the catheter body.

50. A catheter as claimed in claim 1 wherein the reinforcement has a generally rectangular cross-section.

51. A catheter as claimed in claim 50 wherein the reinforcement is aligned with the long side of the rectangle substantially parallel to a radial line which passes through the longitudinal axis of the catheter and the reinforcement.

52. A catheter as claimed in claim 50 wherein the reinforcement is aligned with the short side of the rectangle substantially parallel to a radial line which passes through the longitudinal axis of the catheter and the reinforcement.

53. A catheter as claimed in claim 1 wherein the reinforcement has a generally "I" shaped cross-section.

54. A catheter as claimed in claim 53 wherein the reinforcement is aligned with the end parts of the "I" substantially parallel to a radial line which passes through the longitudinal axis of the catheter and the reinforcement.

55. A catheter as claimed in claim 1 wherein the reinforcement has a generally round cross-section.

56. A catheter as claimed in claim 1 wherein the reinforcement has a generally annular cross-section.

57. A catheter as claimed in claim 1 wherein the cross-sectional area of the reinforcement is small relative to the cross-sectional area of the catheter body.

58. A catheter as claimed in claim 1 wherein the cross-sectional area of the reinforcement and/or of the catheter body varies along the length of the catheter.

59. A catheter as claimed in claim 1 wherein the mechanical properties of the reinforcement and/or of the catheter body varies along the length of the catheter.

60. A catheter as claimed in claim 1 wherein the catheter comprises a guide to facilitate ease of relative movement of the catheter.

61. A catheter as claimed in claim 60 wherein the guide is provided at least partially on an external surface of the catheter.

62. A catheter as claimed in claim 60 wherein the guide is provided at least partially on an internal surface of the catheter.

63. A catheter as claimed in claim 60 wherein the guide extends along the catheter.

64. A catheter as claimed in claim 60 wherein the guide extends at least partially circumferentially around the catheter.

65. A catheter as claimed in claim 60 wherein the guide comprises one or more protrusions on the catheter.

66. A catheter as claimed in claim 65 wherein the protrusion is provided at least partially by the reinforcement.

67. A catheter as claimed in claim 65 wherein the protrusion is provided at least partially by the catheter body.

68. A catheter as claimed in claim 65 wherein the protrusion is shaped for a smooth crossing profile.

69. A catheter as claimed in claim 60 wherein the guide comprises a sheath.

70. A catheter as claimed in claim 1 wherein the catheter comprises at least one reinforcement column extending along the catheter body.

71. A catheter as claimed in claim 70 wherein the column extends at least partially longitudinally along the catheter body.

72. A catheter as claimed in claim 70 wherein the column extends along the catheter body at least partially in a spiral.

73. A catheter as claimed in claim 70 wherein the column is at least partially embedded in the catheter body.

74. A catheter as claimed in claim 71 wherein the column is provided at least partially on an external surface of the catheter body.

75. A catheter as claimed in claim 70 wherein the column is provided at least partially on an internal surface of the catheter body.

76. A catheter as claimed in claim 1 wherein the catheter comprises means to centre the catheter during advancement through a body passageway.

77. A catheter as claimed in claim 77 wherein the centring means comprises a centring catheter for protruding distally of a distal end of the catheter.

78. A catheter as claimed in claim 77 wherein the centring catheter is retractable relative to the catheter.

79. A catheter as claimed in claim 77 wherein the centring catheter has a tip shaped for a smooth crossing profile.

80. A catheter as claimed in claim 79 wherein the tip is arrow-head shaped, or rounded, or ball-nose shaped.

81. A catheter as claimed in claim 1 wherein the catheter is configured to facilitate rapid exchange of the catheter over a guidewire.

82. A catheter as claimed in claim 81 wherein the catheter comprises a guidewire lumen extending partially through the catheter from a distal end of the catheter to a rapid exchange port.

83. A catheter as claimed in claim 82 wherein the reinforcements extend along the catheter body distally of the rapid exchange port.

84. A catheter as claimed in claim 1 wherein the catheter comprises a hydrophilic coating.

85. A catheter as claimed in claim 1 wherein the catheter is an intravascular catheter.

86. A catheter as claimed in claim 1 wherein the catheter is a retrieval catheter.

87. A catheter as claimed in claim 1 wherein the catheter is a delivery catheter.

88. A catheter for advancement through a body passageway, the catheter comprising:
   a flexible catheter body; and
   two reinforcements extending at least partially along the catheter body;
   the two reinforcements being located on opposite sides of the longitudinal axis of the catheter,
   the product $(EI_{max})_R$ of the Young's modulus and the maximum second moment of area of the reinforcement is greater than the product $(EI)_m$ of the Young's modulus and the second moment of area of the catheter body material, and
   $(EI)_m$ is greater than the product $(EI_{min})_R$ of the Young's modulus and the minimum second moment of area of the reinforcement.

89. A catheter as claimed in claim 88 wherein the reinforcement has a generally rectangular cross-section.

90. A catheter as claimed in claim 89 wherein the reinforcement is aligned with the short side of the rectangle substantially parallel to a radial line which passes through the longitudinal axis of the catheter and the reinforcement.

91. A catheter for advancement through a body passageway, the catheter comprising:
   a flexible catheter body; and
   two reinforcements extending at least partially along the catheter body;
   the two reinforcements being located on opposite sides of the longitudinal axis of the catheter,
   the product $(EI_{max})_R$ of the Young's modulus and the maximum second moment of area of the reinforcement is greater than the product $(EI)_m$ of the Young's modulus and the second moment of area of the catheter body material, and
   the Young's modulus of the reinforcement $E_R$ is at least 20 times greater than the Young's modulus of the catheter body material $E_m$.

92. A catheter as claimed in claim 91 wherein the reinforcement has a generally rectangular cross-section.

93. A catheter as claimed in claim 92 wherein the reinforcement is aligned with the short side of the rectangle substantially parallel to a radial line which passes through the longitudinal axis of the catheter and the reinforcement.

* * * * *